US006175000B1

(12) United States Patent
Evans et al.

(10) Patent No.: US 6,175,000 B1
(45) Date of Patent: Jan. 16, 2001

(54) NUCLEIC ACIDS ENCODING HUMAN TRITHORAX PROTEIN

(75) Inventors: Glen A. Evans, Encinitas, CA (US); Malek Djabali, Marseilles (FR); Licia Selleri, Del Mar; Pauline Parry, San Diego, both of CA (US)

(73) Assignee: The Salk Institute for Biological Studies, La Jolla, CA (US)

( * ) Notice: Under 35 U.S.C. 154(b), the term of this patent shall be extended for 0 days.

(21) Appl. No.: 08/061,376

(22) Filed: May 13, 1993

Related U.S. Application Data

(63) Continuation-in-part of application No. 07/954,112, filed on Sep. 30, 1992, now abandoned.

(51) Int. Cl.[7] .......................... C07H 21/04; C07H 21/02; C12Q 1/68

(52) U.S. Cl. .................. 536/23.1; 536/24.31; 536/24.33; 435/6

(58) Field of Search .................... 435/6, 91.1; 536/18.7, 536/23.1, 24.31, 24.33

(56) References Cited

U.S. PATENT DOCUMENTS

| | | | |
|---|---|---|---|
| 5,087,617 | 2/1992 | Smith | 514/44 |
| 5,633,135 | * 5/1997 | Croce et al. | 435/6 |
| 5,633,136 | * 5/1997 | Croce et al. | 435/6 |

OTHER PUBLICATIONS

GCG Oligomer search of SEQ10 No. 1–4, wordsize 15, Genbank–EMBL.*
Saechi et al. Science 231:379 (1986).*
Savage et al. Cytogen Cell Gen. 49:289 (1988).*
Tsujimoto et al. Science 224:1403 (1984).*
Bowden et al. Gene:71:391 (1988).*
Strong et al. Blood 66:439 (1985).*
Cohen et al. Blood 78:94 (1991).*
Gu et al P.N.A.S. 89:10464 (1992).*
Yunis et al. Genomics:5:84 (1989).*
Djabali et al. Nat. Genet. 2:113 (1992).*
Berger et al., "Acute Monocytic Leukemia Chromosome Studies" *Leukemia Research* 6(1):17–26 (1982).
Mazo et al., The Trithorax Gene, A Trans–Acting Regulator Of The Bithorax Complex In Drosophila, Encodes A Protein With Zinc–Binding Domains *Proc. Natl. Acad. Sci. (USA)* 87:2112–2116 (1990).
Sait et al., "A t(1;11) In Acute Nonlymphocytic Leukemia FAB Type M4" *Cancer Genet. Cytogenet.* 24:181–183 (1987).
Feder et al., "A 2p;11q Chromosome Translocation In Dysmyelopoietic Preleukemia" *Cancer Genet. Cytogenet.* 15:143–150 (1985).
Derre, et al., "In Situ Hybridization Ascertains The Presence Of A Translocation t(6;11) In An Acute Monocytic Leukemia" *Genes. Chrom. Can.* 2:341–344 (1990).
Hagemeijer, et al., "Translocation (9;11)(p21;q23) In Three Cases Of Acute Monoblastic Leukemia" *Cancer Genet. Cytogenet.* 5:95–105 (1982).
Pui, et al., "An Analysis Of Leukemic Cell Chromosomal Features In Infants" *Blood* 69(5):1289–1293 (1987).
Abe, et al., "Cytogenetic Findings In Congenital Leukemia: Case Report And Review Of The Literature" *Cancer Genet. Cytogenet.* 9:139–144 (1983).
Chuu, et al., "Infant Leukemia: An Analysis Of Nine Chinese Patients" *Amer. J. Hematol.* 34:246–251 (1990).
Gibbons, et al., "Infant Acute Lymphoblastic Leukaemia With t(11;19)" *British J. Haematology* 74:264–269 (1990).
Rowley, et al., "Mapping Chromosome Band 11q23 In Human Acute Leukemia With Biotinylated Probes: Identification of 11q23 Translocation Breakpoints With A Yeast Artificial Chromosome" *Proc. Natl. Acad. Sci. (USA)* 87:9358–9362 (1990).
Cimino, et al., "Cloning of ALL–1, The Locus Involved In Leukemias With The t(4;11)(q21;q23), t(9;11)(p22;q23), and t(11;19)(q23;p13) Chromosome Translocations[1]" *Cancer Res.* 51:6712–6714 (1991).
Ziemin–Van der Poel, et al., "Identification Of A Gene, MLL, That Spans The Breakpoint in 11q23 Translocations Associated With Human Leukemias" *Proc. Natl. Acad. Sci. (USA)* 88:10735–10739 (1991).
Cimino et al., "An Altered 11–Kilobase Transcript In Leukemia Cell Lines With The t(4;11)(q21;q23) Chromosome Translocation[1]" *Cancer Research* 52:3811–3813 (1992).
Burke, et al., "Cloning of Large Segments Of Exogenous DNA Into Yeast By Means Of Artificial Chromosome Vectors" *Science* 236:806–812 (1987).
O'Connor, et al., "Construction Of Large DNA Segments in Escherichia coli" *Science* 16:1307–1312 (1989).

(List continued on next page.)

Primary Examiner—Stephanie W. Zitomer
(74) Attorney, Agent, or Firm—Gray Cary Ware & Freidenrich; Stephen E. Reiter

(57) ABSTRACT

In accordance with the present invention, there is provided an isolated peptide having the characteristics of human trithorax protein (as well as DNA encoding same, antisense DNA derived therefrom and antagonists therefor). The invention peptide is characterized by having a DNA binding domain comprising multiple zinc fingers and at least 40% amino acid identity with respect to the DNA binding domain of *Drosophila trithorax* protein and at least 70% conserved sequence with respect to the DNA binding domain of *Drosophila trithorax* protein, and wherein said peptide is encoded by a gene located at chromosome 11 of the human genome at q23. Also provided are methods for the treatment of subject(s) suffering from immunodeficiency, developmental abnormality, inherited disease, or cancer by administering to said subject a therapeutically effective amount of one of the above-described agents (i.e., peptide, antagonist therefor, DNA encoding said peptide or antisense DNA derived therefrom). Also provided is a method for the diagnosis, in a subject, of immunodeficiency, developmental abnormality, inherited disease, or cancer associated with disruption of chromosome 11 at q23.

10 Claims, 5 Drawing Sheets

OTHER PUBLICATIONS

Sternberg, N., "Bacteriophage P1 Cloning System For The Isolation, Amplification, And Recovery Of DNA Fragments As Large As 100 Kilobase Pairs" *Proc. Natl. Acad. Sci. (USA)* 87:103–107 (1990).

Evans, et al., "High Efficiency Vectors For Cosmid Microcloning And Genomic Analysis" *Gene* 79:9–20 (1989).

Evans, et al., "Cosmid Vectors For Genomic Walking And Rapid Restriction Mapping" *Methods in Enzymology*, 152:604–610 (1987).

Lichter, et al., "High–Resolution Mapping of Human Chromosome 11 By In Situ Hybridization With Cosmid Clones" *Science* 247:64–69 (1990).

Lawrence, et al., "Sensitive, High–Resolution Chromatin and Chromosome Mapping In Situ: Presence And Orientation Of Two Closely Integrated Copies Of EBV In A Lymphoma Line" *Cell* 52:51–61 (1988).

Pinkel, et al., "Cytogenetic Analysis Using Quantitative, High–Sensitivity, Fluorescence Hybridization" *Proc. Natl. Acad. Sci. (USA)* 83:2934–2938 (1986).

Trask, et al., "The Proximity Of DNA Sequences In Interphase Cell Nuclei Is Correlated To Genomic Distance And Permits Ordering Of Cosmids Spanning 250 Kilobase Pairs[1]" *Genomics* 5:710–717 (1989).

Van Dilla, et al., "Human Chromosome–Specific DNA Libraries: Construction And Availability" *Bio/Technology* 4:537–552 (1986).

Lichter, et al., "Delineation Of Individual Human Chromosomes In Metaphase And Interphase Cells By In Situ Suppression Hybridization Using Recombinant DNA Libraries" *Hum. Genet.* 80:224–234 (1988).

Schweizer, D., "Counterstain–Enhanced Chromosome Banding" *Hum. Genet.* 57:1–14 (1981).

Brownstein, et al., "Isolation Of Single–Copy Human Genes From A Library Of Yeast Artificial Chromosome Clones" *Science* 144:1348–1351 (1989).

Albertsen, et al., "Construction and Characterization Of A Yeast Artificial Chromosome Library Containing Seven Haploid Human Genome Equivalents" *Proc. Natl. Acad. Sci. (USA)* 87:4256–4260 (1990).

Green, et al., "Systematic Screening Of Yeast Artificial–Chromosome Libraries By Use of The Polymerase Chain Reaction" *Proc. Natl. Acad. Sci. (USA)* 87:1213–1217 (1990).

Djabali, et al., "A Simple Method For The Direct Use Of Total Cosmid Clones As Hybridization Probes" *Nucleic Acids Research* 18(20):6166 (1990).

Selleri, et al., "Molecular Localization Of The t(11;22)(q24;q12) Translocation Of Ewing Sarcoma By Chromosomal In Situ Suppression Hybridization" *Proc. Natl. Acad. Sci. (USA)* 88:887–891 (1991).

Benton, et al., "Screening λgt Recombinant Clones By Hybridization To Single Plaques In Situ" *Science* 196:180–182 (1977).

Evans, et al., "Physical Mapping Of Complex Genomes By Cosmid Multiplex Analysis" *Proc. Natl. Acad. Sci. (USA)* 86:5030–5034 (1989).

Chen, et al., "Breakpoint Clustering In t(4;11)(q21;q23) Acute Leukemia" *Blood* 78(10):2498–2504 (1991).

Shafit–Zagardo, et al., "KpnI Families Of Long, Interspersed Repetitive DNAs In Human And Other Primate Genomes" *Nucleic Acids Research* 10(10):3175–3193 (1982).

Altschul, et al., "Basic Local Alignment Search Tool" *J. Mol. Biol.* 215:403–410 (1990).

Zelenetz et al., "Enhancement Detection of the t(14;18) Translocation in Malignant Lymphoma Using Pulsed–Field Gel Electrophoresis" *Blood* 78(6):1552–1560 (1991).

Gu et al., "The t(4;11) Chromosome Translocation of Human Acute Leukemias Fuses the All–1 Gene, Related to Drosophila trithorax, to the AF–4 Gene" *Cell* 71:701–708 (1992).

Tkachuk et al., "Involvement of a Homolog of Drosophila Trithorax by 11q23 Chromosomal Translocations in Acute Leukemias" *Cell* 71:691–700 (1992).

* cited by examiner

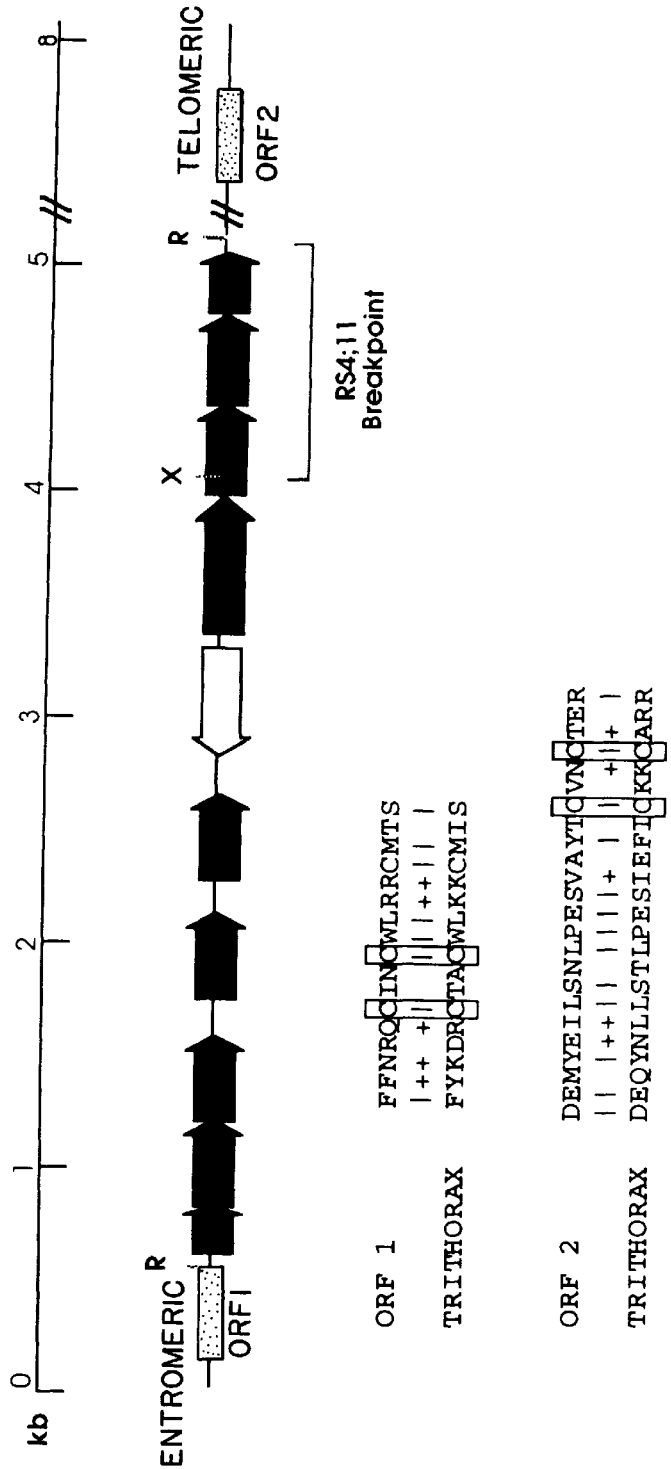

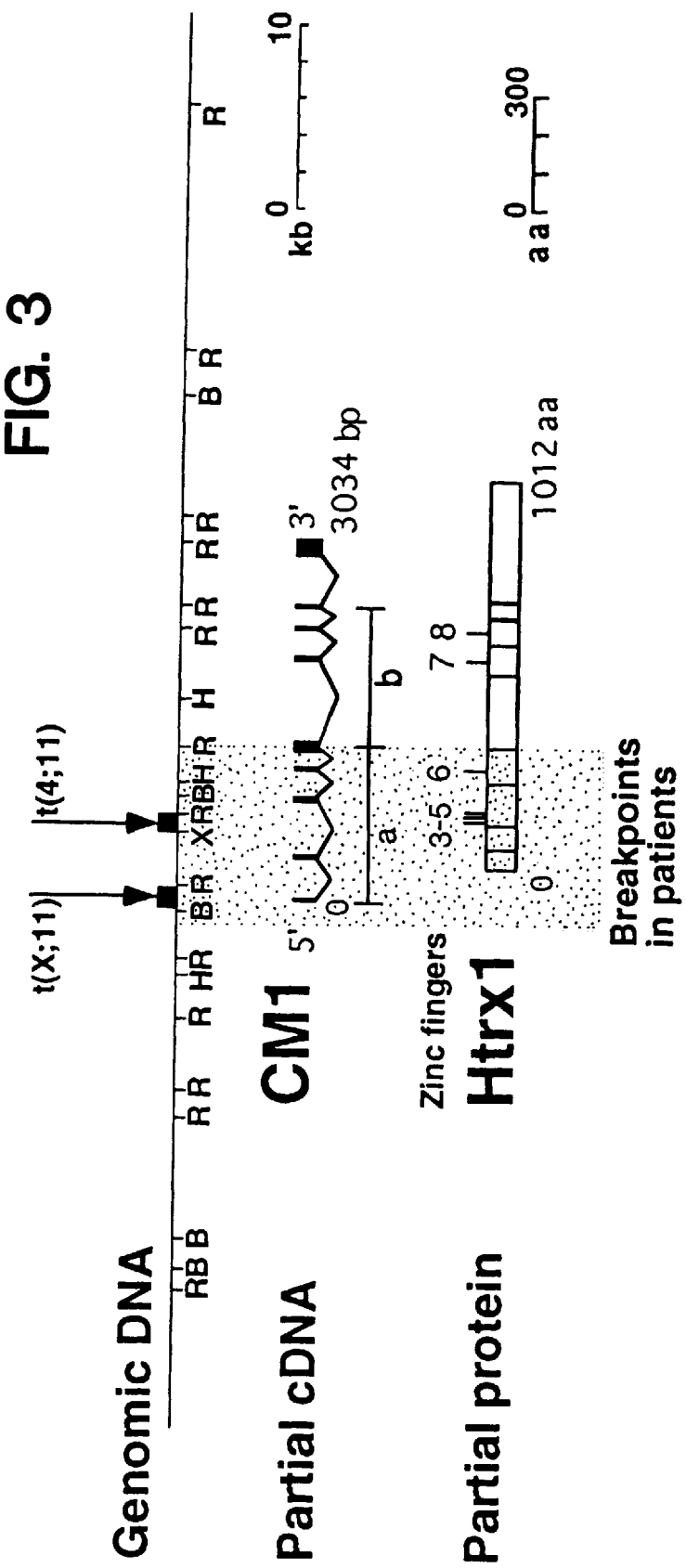

| | | | | | |
|---|---|---|---|---|---|
| 3 | | | | | 1304 |
| 4 | | | | | 1370 |
| 5 | | | | | 1414 |
| 6 | | | | | 1454 |
| 7 | | | | | 1737 |
| 8 | | | | | 1841 |

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2429 base pairs
      (B) TYPE: nucleic acid (C) STRANDEDNESS: both
(D) TOPOLOGY: both (ii) MOLECULE TYPE: DNA (genomic)

(xi) SEQUENCE DESCRIPTION: SEQ ID NO:1:

| | | | | | |
|---|---|---|---|---|---|
| GAATTCCGAA | AGAAGTTCCC | AAAACCACTC | CTAGTGAGCC | CAAGAAAAAG | CAGCCTCCAC | 60 |
| CACCAGAATC | AGGTCCAGAG | CAGAGCAAAC | AGAAAAAAGT | GGCTCCCCGC | CCAAGTATCC | 120 |
| CTGTAAAACA | AAAACCAAAA | GAAAAGGAAA | AACCACCTCC | GGTCAATAAG | CAGGAGAATG | 180 |
| CAGGCACTTT | GAACATCCTC | AGCACTCTCT | CCAATGGCAA | TAGTTCTAAG | CAAAAAATTC | 240 |
| CAGCAGATGG | AGTCCACAGG | ATCAGAGTGG | ACTTTAAGGA | GGATTGTGAA | GCAGAAAATG | 300 |
| TGTGGGAGAT | GGGAGGCTTA | GGAATCTTGA | CTTCTGTTCC | TATAACACCC | AGGGTGGTTT | 360 |
| GCTTTCTCTG | TGCCAGTAGT | GGGCATGTAG | AGTTTGTGTA | TTGCCAAGTC | TGTTGTGAGC | 420 |
| CCTTCCACAA | GTTTTGTTTA | GAGGAGAACG | AGCGCCCTCT | GGAGGACCAG | CTGGAAAATT | 480 |
| GGTGTTGTCG | TCGTTGCAAA | TTCTGTCACG | TTTGTGGAAG | GCAACATCAG | GCTACAAAGC | 540 |
| AGCTGCTGGA | GTGTAATAAG | TGCCGAAACA | GCTATCACCC | TGAGTGCCTG | GACCAAACT | 600 |
| ACCCCACCAA | ACCCACAAAG | AAGAAGAAAG | TCTGGATCTG | TACCAAGTGT | GTTCGCTGTA | 660 |
| AGAGCTGTGG | ATCCACAACN | CCAGGCAAAG | GGTGGGATGC | ACAGTGGTCT | CATGATTTCT | 720 |
| CACTGTNTCA | TGATTGCGCC | AAGCTCTTTG | CTAAAGGAAA | CTTCTGCCCT | CTCTGTGACA | 780 |
| AATGTTATGA | TGATGATGAC | TATGAGAGTA | AGATGATGCA | ATGTGGAAAG | TGTGATCGCT | 840 |
| GGGTCCATTC | CAAATGTGAG | AATCTTTCAG | ATGAGATGTA | TGAGATTCTA | TCTAATCTGC | 900 |
| CAGAAAGTGT | GGCCTACACT | TGTGTGAACT | GTACTGAGCG | GCACCCTGCA | GAGTGGCGAC | 960 |
| TGGCCCTTGA | AAAAGAGCTG | CAGATTTCTC | TGAAGCAAGT | TCTGACAGCT | TTTGTTGAAT | 1020 |
| TCTCGGACTA | CCCAGCCATT | TGCTACGGTA | CCGGCAAGCC | TGCCAAGCTC | CAGACTTAAA | 1080 |
| TCCCGAAGAC | AAGAGGAGAG | ATACCTTNCC | GAAGTTCCCC | CGAAGGCCCT | GATCCACCAG | 1140 |
| TNTTACTTAA | GGCAACAAAC | ANGGGTGCCA | ACAGCCTTAG | NCCTNGAAGG | GCAAGAGGAG | 1200 |
| GTTGCCCAGG | NTGNGCAGCT | TTNANCAGGG | NAACAGCTNA | NNTGNAATCT | NCNAAAACCA | 1260 |
| GGACCACCGT | GGTTNCTGNC | NCACACCTGN | ACCAGCAACT | ANCACCTNCA | TGTGTCCCCG | 1320 |
| AGCCAAGAAC | TGTGNCTTCT | GGATGATAAA | AAAAGTATAT | TGCCAACGAC | ATCGGGATTT | 1380 |
| GATCAAAGGC | GAAAGTGGTC | CNANAATGGA | TTTGAAGTTT | TCAGAAGAAG | TGTTTGTGGA | 1440 |
| CTTTGAAGGA | ATCAGCTTGA | GAAGGGAAGT | TTCTCAATGG | CTTGGAACCA | GAAAATATCC | 1500 |
| ACATGATGAT | TGGGNCTATG | ACAATCGACT | GCTTAGGAAT | TCTAAATGAT | CTCTCCGACT | 1560 |
| GTGAAGATAA | GCTCTTTCCT | ATTGGATATC | AGTGTCCCAG | GGTATACTGG | AGCACCACAG | 1620 |
| ATGCTCGCAA | GCGCTGTGTA | TATACATGCA | AGATAGTGGA | GTGCCGTCCT | CCAGTCGTAG | 1680 |
| AGCCGGATAT | CAACAGCACT | GTTGAACATG | ATGAAAACAG | GACCATTGCC | CATAGTCCAA | 1740 |
| CATCTTTTAC | AGAAAGTTCA | TCAAAGAGA | GTCAAAACAC | AGCTGAAATT | ATAAGTCCTC | 1800 |
| CATCACCAGA | CCGACCTCCT | CATTCACAAA | CCTCTGGCTC | CTGTTATTAT | CATGTCATCT | 1860 |
| CAAAGGTCCC | CAGGATTCGA | ACACCCAGTT | ATTCTCCAAC | ACAGAGATCC | CCTGGCTGTC | 1920 |
| GACCGTTGCC | TTCTGCAGGA | AGTCCTACCC | CAACCACTCA | TGAAATAGTC | ACAGTGAGGT | 1980 |
| GATTCTTTAC | TCTCCTCTGG | ACTTCGAAGC | ATTGGCNCCA | GGCGTCACAG | TACCTCTTCC | 2040 |
| TTATCACCCC | AGCGGTCCAA | ACTCCGGATA | ATGTCTCCAA | TGAACTGG | GAATACTTAC | 2100 |
| TCTAGGAATA | ATGTTTCCTC | AGTCTCCACC | ACCGGGACCG | CTACTGATCT | TGAATCAAGT | 2160 |

```
GCCAAAGTAG TTGATCATGT CTTAGGGCCA CTGAATTCAA GTACTAGTTT AGGGCAAAAC    2220

ACTTCCACCT CTTCAAATTT GCAAAGGACA GTGGTTACTG TAGGCAATAA AAACAGTTCA    2280

CTTGGATGGA TCTTCATCTT CAGAAATGAA GCAGTCCAGT GCTTCAGACT TGGTGTCCAA    2340

GAGCTCCTCT TTAAAGGGAG AGAAGACCAA AGTGCTGAGT TCCAAGAGCT CAGAGGGATC    2400

TGCACATAAT GTGGCTTACC CTGGAATTC                                     2429

(2) INFORMATION FOR SEQ ID NO:2:

(i) SEQUENCE CHARACTERISTICS:
        (A) LENGTH: 1147 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:2:

GAATTCCGAA AGAAGTTCCC AAAACCACTC CTAGTGAGCC CAAGAAAAAG CAGCCTCCAC    60

CACCAGAATC AGGTCCAGAG CAGAGCAAAC AGAAAAAAGT GGCTCCCCGC CCAAGTATCC    120

CTGTAAAACA AAAACCAAAA GAAAAGGAAA AACCACCTCC GGTCAATAAG CAGGAGAATG    180

CAGGCACTTT GAACATCCTC AGCACTCTCT CCAATGGCAA TAGTTCTAAG CAAAAAATTC    240

CAGCAGATGG AGTCCACAGG ATCAGAGTGG ACTTTAAGGA GGATTGTGAA GCAGAAAATG    300

TGTGGGAGAT GGGAGGCTTA GGAATCTTGA CTTCTGTTCC TATAACACCC AGGGTGGTTT    360

GCTTTCTCTG TGCCAGTAGT GGGCATGTAG AGTTTGTGTA TTGCCAAGTC TGTTGTGAGC    420

CCTTCCACAA GTTTTGTTTA GAGGAGAACG AGCGCCCTCT GGAGGACCAG CTGGAAAATT    480

GGTGTTGTCG TCGTTGCAAA TTCTGTCACG TTTGTGGAAG GCAACATCAG GCTACAAAGC    540

AGCTGCTGGA GTGTAATAAG TGCCGAAACA GCTATCACCC TGAGTGCCTG GGACCAAACT    600

ACCCCACCAA ACCCACAAAG AAGAAGAAAG TCTGGATCTG TACCAAGTGT GTTCGCTGTA    660

AGAGCTGTGG ATCCACAACN CCAGGCAAAG GGTGGGATGC ACAGTGGTCT CATGATTTCT    720

CACTGTNTCA TGATTGCGCC AAGCTCTTTG CTAAAGGAAA CTTCTGCCCT CTCTGTGACA    780

AATGTTATGA TGATGATGAC TATGAGAGTA AGATGATGCA ATGTGGAAAG TGTGATCGCT    840

GGGTCCATTC CAAATGTGAG AATCTTTCAG ATGAGATGTA TGAGATTCTA TCTAATCTGC    900

CAGAAAGTGT GGCCTACACT TGTGTGAACT GTACTGAGCG GCACCCTGCA GAGTGGCGAC    960

TGGCCCTTGA AAAAGAGCTG CAGATTTCTC TGAAGCAAGT TCTGACAGCT TTTGTTGAAT    1020

TCTCGGACTA CCCAGCCATT TGCTACGGTA CCGGCAAGCC TGCCAAGCTC CAGACTTAAA    1080

TCCCGAAGAC AAGAGGAGAG ATACCTTNCC GAAGTTCCCC GAAGGCCCT GATCCACCAG    1140

TNTTACT                                                             1147

(2) INFORMATION FOR SEQ ID NO:3:

(i) SEQUENCE CHARACTERISTICS:
        (A) LENGTH: 1208 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:3:

TNANCAGGGN AACAGCTNAN NTGNAATCTN CNAAAACCAG GACCACCGTG GTTNCTGNCN    60

CACACCTGNA CCAGCAACTA NCACCTNCAT GTGTCCCCGA GCCAAGAACT GTGNCTTCTG    120
```

```
GATGATAAAA AAAGTATATT GCCAACGACA TCGGGATTTG ATCAAAGGCG AAAGTGGTCC      180

NANAATGGAT TTGAAGTTTT CAGAAGAAGT GTTTGTGGAC TTTGAAGGAA TCAGCTTGAG      240

AAGGGAAGTT TCTCAATGGC TTGGAACCAG AAAATATCCA CATGATGATT GGGNCTATGA      300

CAATCGACTG CTTAGGAATT CTAAATGATC TCTCCGACTG TGAAGATAAG CTCTTTCCTA      360

TTGGATATCA GTGTCCCAGG GTATACTGGA GCACCACAGA TGCTCGCAAG CGCTGTGTAT      420

ATACATGCAA GATAGTGGAG TGCCGTCCTC CAGTCGTAGA GCCGGATATC AACAGCACTG      480

TTGAACATGA TGAAAACAGG ACCATTGCCC ATAGTCCAAC ATCTTTTACA GAAAGTTCAT      540

CAAAAGAGAG TCAAAACACA GCTGAAATTA TAAGTCCTCC ATCACCAGAC CGACCTCCTC      600

ATTCACAAAC CTCTGGCTCC TGTTATTATC ATGTCATCTC AAAGGTCCCC AGGATTCGAA      660

CACCCAGTTA TTCTCCAACA CAGAGATCCC CTGGCTGTCG ACCGTTGCCT TCTGCAGGAA      720

GTCCTACCCC AACCACTCAT GAAATAGTCA CAGTGAGGTG ATTCTTTACT CTCCTCTGGA      780

CTTCGAAGCA TTGGCNCCAG GCGTCACAGT ACCTCTTCCT TATCACCCCA GCGGTCCAAA      840

CTCCGGATAA TGTCTCCAAT GAGAACTGGG AATACTTACT CTAGGAATAA TGTTTCCTCA      900

GTCTCCACCA CCGGGACCGC TACTGATCTT GAATCAAGTG CCAAAGTAGT TGATCATGTC      960

TTAGGGCCAC TGAATTCAAG TACTAGTTTA GGGCAAAACA CTTCCACCTC TTCAAATTTG     1020

CAAAGGACAG TGGTTACTGT AGGCAATAAA AACAGTTCAC TTGGATGGAT CTTCATCTTC     1080

AGAAATGAAG CAGTCCAGTG CTTCAGACTT GGTGTCCAAG AGCTCCTCTT TAAAGGGAGA     1140

GAAGACCAAA GTGCTGAGTT CCAAGAGCTC AGAGGGATCT GCACATAATG TGGCTTACCC     1200

TGGAATTC                                                             1208

(2) INFORMATION FOR SEQ ID NO:4:

(i) SEQUENCE CHARACTERISTICS:
        (A) LENGTH: 11907 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:4:

ATGGCGCACA GCTGTCGGTG GCGCTTCCCC GCCCGACCCG GACCACCGG GGGCGGCGGC        60

GGCGGGGGC GCCGGGGCCT AGGGGGCGAC CCGCGGCAAC GCGTCCCGGC CCTGCTGCTT       120

CCCCCCGGGC CCCCGGTCGG CGGTGGCGGC CCCGGGGCGC CCCCCTCCCC CCCGGCTGTG      180

GCGGCCGCGG CGGCGGCGGC GGGAAGCAGC GGGGCTGGGG TTCCAGGGGG AGCGGCCGCC      240

GCCTCAGCAG CCTCCTCGTC GTCCGCCTCG TCTTCGTCTT CGTCATCGTC CTCAGCCTCT      300

TCAGGGCCGG CCCTGCTCCG GGTGGGCCCG GGCTTCGACG CGGCGCTGCA GGTCTCGGCC      360

GCCATCGGCA CCAACCTGCG CCGGTTCCGG GCCGTGTTTG GGGAGAGCGG CGGGGGAGGC      420

GGCAGCGGAG AGGATGAGCA ATTCTTAGGT TTTGGCTCAG ATGAAGAAGT CAGAGTGCGA      480

AGTCCCACAA GGTCTCCTTC AGTTAAAACT AGTCCTCGAA AACCTCGTGG GAGACCTAGA      540

AGTGGCTCTG ACCGAAATTC AGCTATCCTC TCAGATCCAT CTGTGTTTTC CCCTCTAAAT      600

AAATCAGAGA CCAAATCTGG AGATAAGATC AAGAAGAAAG ATTCTAAAAG TATAGAAAAG      660

AAGAGAGGAA GACCTCCCAC CTTCCCTGGA GTAAAAATCA AATAACACA TGGAAAGGAC       720

ATTTCAGAGT TACCAAAGGG AAACAAAGAA GATAGCCTGA AAAAAATTAA AAGGACACCT      780

TCTGCTACGT TTCAGCAAGC CACAAAGATT AAAAAATTAA GAGCAGGTAA ACTCTCTCCT      840
```

-continued

```
TCAAGTCTAA GTTAAGACA GGGAAGCTTC AAATAGGAAG GAAGGGGGTA CAAATTGTAG      900
ACGGAGAGGA AGGCCTCCAT CAACAGAAAG GATAAAGACC CCTTCGGTCT CCTCATTATT     960
CTGAACTGGA AAAGCCCCAG AAAGTCCGGA AGACAAGGA AGGAACACCT CCACTTACAA     1020
AAGAAGATAA GACAGTTGTC AGACAAAGCC CTCGAAGGAT TAAGCCAGTT AGGATTATTC    1080
CTTCTTCAAA AAGGACAGAT GCAACCATTG CTAAGCAACT CTTACAGAGG GCAAAAAAG     1140
GGGGCTCAAA AGAAAATTGA AAAGAAGCA GCTCAGCTGC AGGGAAGAAA GGTGAAGACA     1200
CAGGTCAAAA ATATTCGACA GTTCATCATG CCTGTTGTCA GTGCTATCTC CTCGCGGATC    1260
ATTAAGACCC CTCGGCGGTT TATAGAGGAT GAGGATTATG ACCCTCCAAT TAAAATTGCC    1320
CGATTAGAGT CTACACCGAA TAGTAGATTC AGTGCCCCGT CCTGTGGATC TTCTGAAAAA    1380
TCAAGTGCAG CTTCTCAGCA CTCCTCTCAA ATGTCTTCAG ACTCCTCTCG ATCTAGTAGC    1440
CCCAGTGTTG ATACCTCCAC AGACTCTCAG GCTTCTGAGG AGATTCAGGT ACTTCCTGAG    1500
GAGCGGAGCG ATACCCCTGA AGTTCATCCT CCACTGCCCA TTTCCCAGTC CCCAGAAAAT    1560
GAGAGTAATG ATAGGAGAAG CAGAAGGTAT TCAGTGTCGG AGAAGTTT TGGATCTAGA     1620
ACGACGAAAA AATTATCAAC TCTACAAAGT GCCCCCAGC AGCAGACCTC CTCGTCTCCA    1680
CCTCCACCTC TGCTGACTCC ACCGCCACCA CTGCAGCCAG CCTCCAGTAT CTCTGACCAC    1740
ACACCTTGGC TTATGCCTCC AACAATCCCC TTAGCATCAC CATTTTTGCC TGCTTCCACT    1800
GCTCCTATGC AAGGGAAGCG AAAATCTATT TTGCGAGAAC CGACATTTAG GTGGACTTCT    1860
TTAAAGCATT CTAGGTCAGA GCCACAATAC TTTTCCTCAG CAAAGTATGC CAAAGAAGGT    1920
CTTATTCGCA AACCAATATT TGATAATTTC CGACCCCTC CACTAACTCC CGAGGACGTT     1980
GGCTTTGCAT CTGGTTTTTC TGCATCTGGT ACCGCTGCTT CAGCCCGATT GTTTTCGCCA    2040
CTCCATTCTG GAACAAGGTT TGATATGCAC AAAAGGAGCC CTCTTCTGAG AGCTCCAAGA    2100
TTTACTCCAA GTGAGGCTCA CTCTAGAATA TTTGAGTCTG TAACCTTGCC TAGTAATCGA    2160
ACTTCTGCTG AACATCTTC TTCAGGAGTA TCCAATAGAA AAAGGAAAAG AAAAGTGTTT    2220
AGTCCTATTC GATCTGAACC AAGATCTCCT TCTCACTCCA TGAGGACAAG AAGTGGAAGG    2280
CTTAGTAGTT CTGAGCTCTC ACCTCTCACC CCCCGTCTT CTGTCTCTTC CTCGTTAAGC     2340
ATTTCTGTTA GTCCTCTTGC CACTAGTGCC TTAAACCCAA CTTTTACTTT TCCTTCTCAT    2400
TCCCTGACTC AGTCTGGGGA ATCTGCAGAG AAAAATCAGA GACCAAGGAA GCAGACTAGT    2460
GCTCCGGCAG AGCCATTTTC ATCAAGTAGT CCTACTCCTC TCTTCCCTTG GTTTACCCCA    2520
GGCTCTCAGA CTGAAAGAGG GAGAAATAAA GACAAGGCCC CCGAGGAGCT GTCCAAAGAT    2580
CGAGATGCTG ACAAGAGCGT GGAGAAGGAC AAGAGTAGAG AGAGAGACCG GGAGAGAGAA    2640
AAGGAGAATA AGCGGGAGTC AAGGAAAGAG AAAAGGAAAA AGGGATCAGA AATTCAGAGT    2700
AGTTCTGCTT TGTATCCTGT GGGTAGGGTT TCCAAAGAGA AGGTTGTTGG TGAAGATGTT    2760
GCCACTTCAT CTTCTGCCAA AAAAGCAACA GGGCGGAAGA AGTCTTCATC ACATGATTCT    2820
GGGACTGATA TTACTTCTGT GACTCTTGGG GATACAACAG CTGTCAAAAC CAAAATACTT    2880
ATAAAGAAAG GGAGAGGAAA TCTGGAAAAA ACCAACTTGG ACCTCGGCCC AACTGCCCCA    2940
TCCCTGGAGA AGGAGAAAAC CCTCTGCCTT TCCACTCCTT CATCTAGCAC TGTTAAACAT    3000
TCCACTTCCT CCATAGGCTC CATGTTGGCT CAGGCAGACA AGCTTCCAAT GACTGACAAG    3060
AGGGTTGCCA GCCTCCTAAA AAAGGCCAAA GCTCAGCTCT GCAAGATTGA GAAGAGTAAG    3120
AGTCTTAAAC AAACCGACCA GCCCAAAGCA CAGGGTCAAG AAAGTGACTC ATCAGAGACC    3180
```

-continued

```
TCTGTGCGAG GACCCCGGAT TAAACATGTC TGCAGAAGAG CAGCTGTTGC CCTTGGCCGA      3240

AAACGAGCTG TGTTTCCTGA TGACATGCCC ACCCTGAGTG CCTTACCATG GAAGAACGA       3300

GAAAAGATTT TGTCTTCCAT GGGGAATGAT GACAAGTCAT CAATTGCTGG CTCAGAAGAT      3360

GCTGAACCTC TTGCTCCACC CATCAAACCA ATTAAACCTG TCACTAGAAA CAAGGCACCC      3420

CAGGAACCTC CAGTAAAGAA AGGACGTCGA TCGAGGCGGT GTGGGCAGTG TCCCGGCTGC      3480

CAGGTGCCTG AGGACTGTGG TGTTTGTACT AATTGCTTAG ATAAGCCCAA GTTTGGTGGT      3540

CGCAATATAA AGAAGCAGTG CTGCAAGATG AGAAAATGTC AGAATCTACA ATGGATGCCT      3600

TCCAAAGCCT ACCTGCAGAA GCAAGCTAAA GCTGTGAAAA AGAAAGAGAA AAAGTCTAAG      3660

ACCAGTGAAA AGAAAGACAG CAAAGAGAGC AGTGTTGTGA AGAACGTGGT GGACTCTAGT     3720

CAGAAACCTA CCCCATCAGC AAGAGAGGAT CCTGCCCCAA AGAAAAGCAG TAGTGAGCCT      3780

CCTCCACGAA AGCCCGTCGA GGAAAAGAGT GAAGAAGGGA ATGTCTCGGC CCCTGGGCCT      3840

GAATCCAAAC AGGCCACCAC TCCAGCTTCC AGGAAGTCAA GCAAGCAGGT CTCCCAGCCA     3900

GCACTGGTCA TCCCGCCTCA GCCACCTACT ACAGGACCGC CAAGAAAAGA AGTTCCCAAA     3960

ACCACTCCTA GTGAGCCCAA GAAAAAGCAG CCTCCACCAC CAGAATCAGG TCCAGAGCAG     4020

AGCAAACAGA AAAAAGTGGC TCCCCGCCCA AGTATCCCTG TAAAACAAAA ACCAAAAGAA     4080

AAGGAAAAAC CACCTCCGGT CAATAAGCAG GAGAATGCAG GCACTTTGAA CATCCTCAGC     4140

ACTCTCTCCA ATGGCAATAG TTCTAAGCAA AAAATTCCAG CAGATGGAGT CCACAGGATC     4200

AGAGTGGACT TTAAGGAGGA TTGTGAAGCA GAAAATGTGT GGGAGATGGG AGGCTTAGGA     4260

ATCTTGACTT CTGTTCCTAT AACACCCAGG GTGGTTTGCT TTCTCTGTGC AGTAGTGGG      4320

CATGTAGAGT TTGTGTATTG CCAAGTCTGT TGTGAGCCCT TCCACAAGTT TTGTTTAGAG     4380

GAGAACGAGC GCCCTCTGGA GGACCAGCTG GAAAATTGGT GTTGTCGTCG TTGCAAATTC     4440

TGTCACGTTT GTGGAAGGCA ACATCAGGCT ACAAAGCAGC TGCTGGAGTG TAATAAGTGC     4500

CGAAACAGCT ATCACCCTGA GTGCCTGGGA CCAAACTACC CCACCAAACC CACAAAGAAG     4560

AAGAAAGTCT GGATCTGTAC CAAGTGTGTT CGCTGTAAGA GCTGTGGATC CACAACTCCA     4620

GGCAAAGGGT GGGATGCACA GTGGTCTCAT GATTTCTCAC TGTGTCATGA TTGCGCCAAG     4680

CTCTTTGCTA AAGGAAACTT CTGCCCTCTC TGTGACAAAT GTTATGATGA TGATGACTAT     4740

GAGAGTAAGA TGATGCAATG TGGAAAGTGT GATCGCTGGG TCCATTCCAA ATGTGAGAAT     4800

CTTTCAGATG AGATGTATGA GATTCTATCT AATCTGCCAG AAAGTGTGGC CTACACTTGT     4860

GTGAACTGTA CTGAGCGGCA CCCTGCAGAG TGGCGACTGG CCCTTGAAAA AGAGCTGCAG     4920

ATTTCTCTGA AGCAAGTTCT GACAGCTTTG TTGAATTCTC GGACTACCAG CCATTTGCTA    4980

CGCTACCGGC AGGCTGCCAA GCCTCCAGAC TTAAATCCCG AGACAGAGGA GAGTATACCT     5040

TCCCGCAGCT CCCCCGAAGG ACCTGATCCA CCAGTTCTTA CTGAGGTCAG CAAACAGGAT    5100

GATCAGCAGC CTTTAGATCT AGAAGGAGTC AAGAGGAAGA TGGACCAAGG GAATTACACA     5160

TCTGTGTTGG AGTTCAGTGA TGATATTGTG AAGATCATTC AAGCAGCCAT TAATTCAGAT     5220

GGAGGACAGC CAGAAATTAA AAAAGCCAAC AGCATGGTCA AGTCCTTCTT CATTCGGCAA     5280

ATGGAACGTG TTTTTCCATG GTTCAGTGTC AAAAAGTCCA GGTTTTGGGA GCCAAATAAA     5340

GTATCAAGCA ACAGTGGGAT GTTACCAAAC GCAGTGCTTC CACCTTCACT TGACCATAAT     5400

TATGCTCAGT GGCAGGAGCG AGAGGAAAAC AGCCACACTG AGCAGCCTCC TTTAATGAAG     5460

AAAATCATTC CAGCTCCCAA ACCCAAAGGT CCTGGAGAAC CAGACTCACC AACTCCTCTG     5520

CATCCTCCTA CACCACCAAT TTTGAGTACT GATAGGAGTC GAGAAGACAG TCCAGAGCTG     5580
```

```
AACCCACCCC CAGGCATAGA AGACAATAGA CAGTGTGCGT TATGTTTGAC TTATGGTGAT    5640

GACAGTGCTA ATGATGCTGG TCGTTTACTA TATATTGGCC AAAATGAGTG GACACATGTA    5700

AATTGTGCTT TGTGGTCAGC GGAAGTGTTT GAAGATGATG ACGGATCACT AAAGAATGTG    5760

CATATGGCTG TGATCAGGGG CAAGCAGCTG AGATGTGAAT TCTGCCAAAA GCCAGGAGCC    5820

ACCGTGGGTT GCTGTCTCAC ATCCTGCACC AGCAACTATC ACTTCATGTG TTCCCGAGCC    5880

AAGAACTGTG TCTTTCTGGA TGATAAAAAA GTATATTGCC AACGACATCG GGATTTGATC    5940

AAAGGCGAAG TGGTTCCTGA GAATGGATTT GAAGTTTTCA GAAGAGTGTT TGTGGACTTT    6000

GAAGGAATCA GCTTGAGAAG GAAGTTTCTC AATGGCTTGG AACCAGAAAA TATCCACATG    6060

ATGATTGGGT CTATGACAAT CGACTGCTTA GGAATTCTAA ATGATCTCTC CGACTGTGAA    6120

GATAAGCTCT TTCCTATTGG ATATCAGTGT TCCAGGGTAT ACTGGAGCAC CACAGATGCT    6180

CGCAAGCGCT GTGTATATAC ATGCAAGATA GTGGAGTGCC GTCCTCCAGT CGTAGAGCCG    6240

GATATCAACA GCACTGTTGA ACATGATGAA ACAGGACCA TTGCCCATAG TCCAACATCT    6300

TTTACAGAAA GTTCATCAAA AGAGAGTCAA AACACAGCTG AAATTATAAG TCCTCCATCA    6360

CCAGACCGAC CTCCTCATTC ACAAACCTCT GGCTCCTGTT ATTATCATGT CATCTCAAAG    6420

GTCCCCAGGA TTCGAACACC CAGTTATTCT CCAACACAGA GATCCCCTGG CTGTCGACCG    6480

TTGCCTTCTG CAGGAAGTCC TACCCCAACC ACTCATGAAA TAGTCACAGT AGGTGATCCT    6540

TTACTCTCCT CTGGACTTCG AAGCATTGGC TCCAGGCGTC ACAGTACCTC TTCCTTATCA    6600

CCCCAGCGGT CCAAACTCCG GATAATGTCT CCAATGAGAA CTGGGAATAC TTACTCTAGG    6660

AATAATGTTT CCTCAGTCTC CACCACCGGG ACCGCTACTG ATCTTGAATC AAGTGCCAAA    6720

GTAGTTGATC ATGTCTTAGG GCCACTGAAT TCAAGTACTA GTTTAGGGCA AAACACTTCC    6780

ACCTCTTCAA ATTTGCAAAG GACAGTGGTT ACTGTAGGCA ATAAAAACAG TCACTTGGAT    6840

GGATCTTCAT CTTCAGAAAT GAAGCAGTCC AGTGCTTCAG ACTTGGTGTC CAAGAGCTCC    6900

TCTTTAAAGG GAGAGAAGAC CAAAGTGCTG AGTTCCAAGA GCTCAGAGGG ATCTGCACAT    6960

AATGTGGCTT ACCCTGGAAT TCCTAAACTG GCCCCACAGG TTCATAACAC AACATCTAGA    7020

GAACTGAATG TTAGTAAAAT CGGCTCCTTT GCTGAACCCT CTTCAGTGTC GTTTTCTTCT    7080

AAAGAGGCCC TCTCCTTCCC ACACCTCCAT TTGAGAGGGC AAAGGAATGA TCGAGACCAA    7140

CACACAGATT CTACCCAATC AGCAAACTCC TCTCCAGATG AAGATACTGA AGTCAAAACC    7200

TTGAAGCTAT CTGGAATGAG CAACAGATCA TCCATTATCA ACGAACATAT GGGATCTAGT    7260

TCCAGAGATA GGGACAGAA AGGGAAAAAA TCCTGTAAAG AAACTTTCAA AGAAAAGCAT    7320

TCCAGTAAAT CTTTTTTGGA ACCTGGTCAG GTGACAACTG GTGAGGAAGG AAACTTGAAG    7380

CCAGAGTTTA TGGATGAGGT TTTGACTCCT GAGTATATGG CCAACGACC ATGTAACAAT    7440

GTTTCTTCTG ATAAGATTGG TGATAAAGGC CTTTCTATGC CAGGAGTCCC CAAAGCTCCA    7500

CCCATGCAAG TAGAAGGATC TGCCAAGGAA TTACAGGCAC ACGGAAACG CACAGTCAAA    7560

GTGACACTGA CACCTCTAAA AATGGAAAAT GAGAGTCAAT CCAAAAATGC CCTGAAAGAA    7620

AGTAGTCCTG CTTCCCCTTT GCAAATAGAG TCAACATCTC CCACAGAACC AATTTCAGCC    7680

TCTGAAAATC CAGGAGATGG TCCAGTGGCC CAACCAAGCC CCAATAATAC CTCATGCCAG    7740

GATTCTCAAA GTAACAACTA TCAGAATCTT CCAGTACAGG ACAGAAACCT AATGCTTCCA    7800

GATGGCCCCA AACCTCAGGA GGATGGCTCT TTTAAAAGGA GGTATCCCCG TCGCAGTGCC    7860

CGTGCACGTT CTAACATGTT TTTTGGGCTT ACCCCACTCT ATGGAGTAAG ATCCTATGGT    7920
```

```
GAAGAAGACA TTCCATTCTA CAGCAGCTCA ACTGGGAAGA AGCGAGGCAA GAGATCAGCT    7980

GAAGGACAGG TGGATGGGGC CGATGACTTA AGCACTTCAG ATGAAGACGA CTTATACTAT    8040

TACAACTTCA CTAGAACAGT GATTTCTTCA GGTGGAGAGG AACGACTGGC ATCCCATAAT    8100

TTATTTCGGG AGGAGGAACA GTGTGATCTT CCAAAAATCT CACAGTTGGA TGGTGTTGAT    8160

GATGGGACAG AGAGTGATAC TAGTGTCACA GCCACAACAA GGAAAAGCAG CCAGATTCCA    8220

AAAAGAAATG GTAAAGAAAA TGGAACAGAG AACTTAAAGA TTGATAGACC TGAAGATGCT    8280

GGGGAGAAAG AACATGTCAC TAAGAGTTCT GTTGGCCACA AAAATGAGCC AAAGATGGAT    8340

AACTGCCATT CTGTAAGCAG AGTTAAAACA CAGGGACAAG ATTCCTTGGA AGCTCAGCTC    8400

AGCTCATTGG AGTCAAGCCG CAGAGTCCAC ACAAGTACCC CCTCCGACAA AAATTTACTG    8460

GACACCTATA ATACTGAGCT CCTGAAATCA GATTCAGACA ATAACAACAG TGATGACTGT    8520

GGGAATATCC TGCCTTCAGA CATTATGGAC TTTGTACTAA AGAATACTCC ATCCATGCAG    8580

GCTTTGGGTG AGAGCCCAGA GTCATCTTCA TCAGAACTCC TGAATCTTGG TGAAGGATTG    8640

GGTCTTGACA GTAATCGTGA AAAAGACATG GGTCTTTTTG AAGTATTTTC TCAGCAGCTG    8700

CCTACAACAG AACCTGTGGA TAGTAGTGTC TCTTCCTCTA TCTCAGCAGA GGAACAGTTT    8760

GAGTTGCCTC TAGAGCTACC ATCTGATCTG TCTGTCTTGA CCACCCGGAG TCCCACTGTC    8820

CCCAGCCAGA ATCCCAGTAG ACTAGCTGTT ATCTCAGACT CAGGGGAGAA GAGAGTAACC    8880

ATCACAGAAA AATCTGTAGC CTCCTCTGAA AGTGACCCAG CACTGCTGAG CCCAGGAGTA    8940

GATCCAACTC CTGAAGGCCA CATGACTCCT GATCATTTTA TCCAAGGACA CATGGATGCA    9000

GACCACATCT CTAGCCCTCC TTGTGGTTCA GTAGAGCAAG GTCATGGCAA CAATCAGGAT    9060

TTAACTAGGA ACAGTAGCAC CCCTGGCCTT CAGGTACCTG TTTCCCCAAC TGTTCCCATC    9120

CAGAACCAGA AGTATGTGCC CAATTCTACT GATAGTCCTG GCCCGTCTCA GATTTCCAAT    9180

GCAGCTGTCC AGACCACTCC ACCCCACCTG AAGCCAGCCA CTGAGAAACT CATAGTTGTT    9240

AACCAGAACA TGCAGCCACT TTATGTTCTC CAAACTCTTC CAAATGGAGT GACCCAAAAA    9300

ATCCAATTGA CCTCTTCTGT TAGTTCTACA CCCAGTGTGA TGGAGACAAA TACTTCAGTA    9360

TTGGGACCCA TGGGAGGTGG TCTCACCCTT ACCACAGGAC TAAATCCAAG CTTGCCAACT    9420

TCTCAATCTT TGTTCCCTTC TGCTAGCAAA GGATTGCTAC CCATGTCTCA TCACCAGCAC    9480

TTACATTCCT TCCCTGCAGC TACTCAAAGT AGTTTCCCAC CAAACATCAG CAATCCTCCT    9540

TCAGGCCTGC TTATTGGGGT TCAGCCTCCT CCGGATCCCC AACTTTTGGT TTCAGAATCC    9600

AGCCAGAGGA CAGACCTCAG TACCACAGTA GCCACTCCAT CCTCTGGACT CAAGAAAAGA    9660

CCCATATCTC GTCTACAGAC CCGAAAGAAT AAAAAACTTG CTCCCTCTAG TACCCCTTCA    9720

AACATTGCCC CTTCTGATGT GGTTTCTAAT ATGACATTGA TTAACTTCAC ACCCTCCCAG    9780

CTTCCTAATC ATCCAAGTCT GTTAGATTTG GGGTCACTTA ATACTTCATC TCACCGAACT    9840

GTCCCCAACA TCATAAAAAG ATCTAAATCT AGCATCATGT ATTTTGAACC GGCACCCCTG    9900

TTACCACAGA GTGTGGGAGG AACTGCTGCC ACAGCGGCAG GCACATCAAC AATAAGCCAG    9960

GATACTAGCC ACCTCACATC AGGGTCTGTG TCTGGCTTGG CATCCAGTTC CTCTGTCTTG   10020

AATGTTGTAT CCATGCAAAC TACCACAACC CCTACAAGTA GTGCGTCAGT TCCAGGACAC   10080

GTCACCTTAA CCAACCCAAG GTTGCTTGGT ACCCCAGATA TTGGCTCAAT AAGCAATCTT   10140

TTAATCAAAG CTAGCCAGCA GAGCCTGGGG ATTCAGGACC AGCCTGTGGC TTTACCGCCA   10200

AGTTCAGGAA TGTTTCCACA ACTGGGGACA TCACAGACCC CCTCTACTGC TGCAATAACA   10260

GCGGCATCTA GCATCTGTGT GCTCCCCTCC ACTCAGACTA CGGGCATAAC AGCCGCTTCA   10320
```

-continued

```
CCTTCTGGGG AAGCAGACGA ACACTATCAG CTTCAGCATG TGAACCAGCT CCTTGCCAGC    10380

AAAACTGGGA TTCATTCTTC CCAGCGTGAT CTTGATTCTG CTTCAGGGCC CCAGGTATCC    10440

AACTTTACCC AGACGGTAGA CGCTCCTAAT AGCATGGGAC TGGAGCAGAA CAAGGCTTTA    10500

TCCTCAGCTG TGCAAGCCAG CCCCACCTCT CCTGGGGGTT CTCCATCCTC TCCATCTTCT    10560

GGACAGCGGT CAGCAAGCCC TTCAGTGCCG GGTCCCACTA AACCCAAACC AAAAACCAAA    10620

CGGTTTCAGC TGCCTCTAGA CAAAGGGAAT GGCAAGAAGC ACAAAGTTTC CCATTTGCGG    10680

ACCAGTTCTT CTGAAGCACA CATTCCAGAC CAAGAAACGA CATCCCTGAC CTCAGGCACA    10740

GGGACTCCAG GAGCAGAGGC TGAGCAGCAG GATACAGCTA GCGTGGAGCA GTCCTCCCAG    10800

AAGGAGTGTG GGCAACCTGC AGGGCAAGTC GCTGTTCTTC CGGAAGTTCA GGTGACCCAA    10860

AATCCAGCAA ATGAACAAGA AAGTGCAGAA CCTAAAACAG TGGAAGAAGA GGAAAGTAAT    10920

TTCAGCTCCC CACTGATGCT TTGGCTTCAG CAAGAACAAA AGCGGAAGGA AAGCATTACT    10980

GAGAAAAAAC CCAAGAAAGG ACTTGTTTTT GAAATTTCCA GTGATGATGG CTTTCAGATC    11040

TGTGCAGAAA GTATTGAAGA TGCCTGGAAG TCATTGACAG ATAAAGTCCA GGAAGCTCGA    11100

TCAAATGCCC GCCTAAAGCA GCTCTCATTT GCAGGTGTTA ACGGTTTGAG GATGCTGGGG    11160

ATTCTCCATG ATGCAGTTGT GTTCCTCATT GAGCAGCTGT CTGGTGCCAA GCACTGTCGA    11220

AATTACAAAT TCCGTTTCCA CAAGCCAGAG GAGGCCAATG AACCCCCCTT GAACCCTCAC    11280

GGCTCAGCCA GGGCTGAAGT CCACCTCAGG AAGTCAGCAT TTGACATGTT TAACTTCCTG    11340

GCTTCTAAAC ATCGTCAGCC TCCTGAATAC AACCCCAATG ATGAAGAAGA GGAGGAGGTA    11400

CAGCTGAAGT CAGCTCGGAG GGCAACTAGC ATGGATCTGC CAATGCCCAT GCGCTTCCGG    11460

CACTTAAAAA AGACTTCTAA GGAGGCAGTT GGTGTCTACA GGTCTCCCAT CCATGGCCGG    11520

GGTCTTTTCT GTAAGAGAAA CATTGATGCA GGTGAGATGG TGATTGAGTA TGCCGGCAAC    11580

GTCATCCGCT CCATCCAGAC TGACAAGCGG GAAAAGTATT ACGACAGCAA GGGCATTGGT    11640

TGCTATATGT TCCGAATTGA TGACTCGAGG GTAGTGGATG CCACCATGCA TGGAAATCGT    11700

GCACGCTTCA TCAATCACTC GTGTGAGCCT AACTGCTATT CTCGGGTCAT CAATATTGAT    11760

GGGCAGAAGC ACATTGTCAT CTTTGCCATG CGTAAGATCT ACCGAGGAGA GGAACTCACT    11820

TACGACTATA AGTTCCCCAT TGAGGATGCC AGCAACAAGC TGCCCTGCAA CTGTGGCGCC    11880

AAGAAATGCC GGAAGTTCCT AAACTAA                                       11907
```

(2) INFORMATION FOR SEQ ID NO:5:

(i) SEQUENCE CHARACTERISTICS:
        (A) LENGTH: 3969 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

```
Met Ala His Ser Cys Arg Trp Arg Phe Pro Ala Arg Pro Gly Thr Thr
 1               5                  10                  15

Gly Gly Gly Gly Gly Gly Gly Arg Arg Gly Leu Gly Gly Asp Pro Arg
            20                  25                  30

Gln Arg Val Pro Ala Leu Leu Leu Pro Pro Gly Pro Val Gly Gly
        35                  40                  45

Gly Gly Pro Gly Ala Pro Pro Ser Pro Ala Val Ala Ala Ala Ala
    50                  55                  60
```

```
Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser Ser
                85                  90                  95

Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
            115                 120                 125

Phe Arg Ala Val Phe Gly Glu Ser Gly Gly Gly Gly Ser Gly Glu
    130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
            180                 185                 190

Pro Ser Val Phe Ser Pro Leu Asn Lys Ser Glu Thr Lys Ser Gly Asp
            195                 200                 205

Lys Ile Lys Lys Lys Asp Ser Lys Ser Ile Glu Lys Lys Arg Gly Arg
210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
            260                 265                 270

Leu Arg Ala Gly Lys Leu Ser Pro Ser Ser Leu Ser Leu Arg Gln Gly
    275                 280                 285

Ser Phe Lys Glx Glu Gly Arg Gly Tyr Lys Leu Glx Thr Glu Arg Lys
    290                 295                 300

Ala Ser Ile Asn Arg Lys Asp Lys Asp Pro Phe Gly Leu Leu Ile Ile
305                 310                 315                 320

Leu Asn Trp Lys Ser Pro Arg Lys Ser Gly Lys Thr Arg Lys Glu His
                325                 330                 335

Leu His Leu Gln Lys Lys Ile Arg Gln Leu Ser Asp Lys Ala Leu Glu
            340                 345                 350

Gly Leu Ser Gln Leu Gly Leu Phe Leu Leu Gln Lys Gly Gln Met Gln
            355                 360                 365

Pro Leu Leu Ser Asn Ser Tyr Arg Gly Gln Lys Lys Gly Ala Gln Lys
    370                 375                 380

Lys Ile Glu Lys Glu Ala Ala Gln Leu Gln Gly Arg Lys Val Lys Thr
385                 390                 395                 400

Gln Val Lys Asn Ile Arg Gln Phe Ile Met Pro Val Val Ser Ala Ile
                405                 410                 415

Ser Ser Arg Ile Ile Lys Thr Pro Arg Arg Phe Ile Glu Asp Glu Asp
            420                 425                 430

Tyr Asp Pro Pro Ile Lys Ile Ala Arg Leu Glu Ser Thr Pro Asn Ser
            435                 440                 445

Arg Phe Ser Ala Pro Ser Cys Gly Ser Ser Glu Lys Ser Ser Ala Ala
    450                 455                 460

Ser Gln His Ser Ser Gln Met Ser Ser Asp Ser Ser Arg Ser Ser Ser
465                 470                 475                 480
```

-continued

```
Pro Ser Val Asp Thr Ser Thr Asp Ser Gln Ala Ser Glu Glu Ile Gln
            485                 490                 495
Val Leu Pro Glu Glu Arg Ser Asp Thr Pro Glu Val His Pro Pro Leu
        500                 505                 510
Pro Ile Ser Gln Ser Pro Glu Asn Glu Ser Asn Asp Arg Arg Ser Arg
        515                 520                 525
Arg Tyr Ser Val Ser Glu Arg Ser Phe Gly Ser Arg Thr Thr Lys Lys
    530                 535                 540
Leu Ser Thr Leu Gln Ser Ala Pro Gln Gln Thr Ser Ser Ser Pro
545                 550                 555                 560
Pro Pro Pro Leu Leu Thr Pro Pro Pro Leu Gln Pro Ala Ser Ser
                565                 570                 575
Ile Ser Asp His Thr Pro Trp Leu Met Pro Pro Thr Ile Pro Leu Ala
            580                 585                 590
Ser Pro Phe Leu Pro Ala Ser Thr Ala Pro Met Gln Gly Lys Arg Lys
        595                 600                 605
Ser Ile Leu Arg Glu Pro Thr Phe Arg Trp Thr Ser Leu Lys His Ser
        610                 615                 620
Arg Ser Glu Pro Gln Tyr Phe Ser Ser Ala Lys Tyr Ala Lys Glu Gly
625                 630                 635                 640
Leu Ile Arg Lys Pro Ile Phe Asp Asn Phe Arg Pro Pro Pro Leu Thr
                645                 650                 655
Pro Glu Asp Val Gly Phe Ala Ser Gly Phe Ser Ala Ser Gly Thr Ala
                660                 665                 670
Ala Ser Ala Arg Leu Phe Ser Pro Leu His Ser Gly Thr Arg Phe Asp
            675                 680                 685
Met His Lys Arg Ser Pro Leu Leu Arg Ala Pro Arg Phe Thr Pro Ser
        690                 695                 700
Glu Ala His Ser Arg Ile Phe Glu Ser Val Thr Leu Pro Ser Asn Arg
705                 710                 715                 720
Thr Ser Ala Gly Thr Ser Ser Gly Val Ser Asn Arg Lys Arg Lys
                725                 730                 735
Arg Lys Val Phe Ser Pro Ile Arg Ser Glu Pro Arg Ser Pro Ser His
                740                 745                 750
Ser Met Arg Thr Arg Ser Gly Arg Leu Ser Ser Glu Leu Ser Pro
            755                 760                 765
Leu Thr Pro Pro Ser Ser Val Ser Ser Ser Leu Ser Ile Ser Val Ser
770                 775                 780
Pro Leu Ala Thr Ser Ala Leu Asn Pro Thr Phe Thr Phe Pro Ser His
785                 790                 795                 800
Ser Leu Thr Gln Ser Gly Glu Ser Ala Glu Lys Asn Gln Arg Pro Arg
                805                 810                 815
Lys Gln Thr Ser Ala Pro Ala Glu Pro Phe Ser Ser Ser Pro Thr
            820                 825                 830
Pro Leu Phe Pro Trp Phe Thr Pro Gly Ser Gln Thr Glu Arg Gly Arg
            835                 840                 845
Asn Lys Asp Lys Ala Pro Glu Glu Leu Ser Lys Asp Arg Asp Ala Asp
        850                 855                 860
Lys Ser Val Glu Lys Asp Lys Ser Arg Glu Arg Asp Arg Glu Arg Glu
865                 870                 875                 880
Lys Glu Asn Lys Arg Glu Ser Arg Lys Glu Arg Lys Lys Gly Ser
                885                 890                 895
Glu Ile Gln Ser Ser Ser Ala Leu Tyr Pro Val Gly Arg Val Ser Lys
```

-continued

```
                900              905              910
Glu Lys Val Val Gly Glu Asp Val Ala Thr Ser Ser Ala Lys Lys
        915              920              925
Ala Thr Gly Arg Lys Ser Ser His Asp Ser Gly Thr Asp Ile
    930              935              940
Thr Ser Val Thr Leu Gly Asp Thr Thr Ala Val Lys Thr Lys Ile Leu
945              950              955              960
Ile Lys Lys Gly Arg Gly Asn Leu Glu Lys Thr Asn Leu Asp Leu Gly
                965              970              975
Pro Thr Ala Pro Ser Leu Glu Lys Glu Lys Thr Leu Cys Leu Ser Thr
            980              985              990
Pro Ser Ser Ser Thr Val Lys His Ser Thr Ser Ser Ile Gly Ser Met
            995              1000             1005
Leu Ala Gln Ala Asp Lys Leu Pro Met Thr Asp Lys Arg Val Ala Ser
        1010             1015             1020
Leu Leu Lys Lys Ala Lys Ala Gln Leu Cys Lys Ile Glu Lys Ser Lys
1025             1030             1035             1040
Ser Leu Lys Gln Thr Asp Gln Pro Lys Ala Gln Gly Gln Glu Ser Asp
                1045             1050             1055
Ser Ser Glu Thr Ser Val Arg Gly Pro Arg Ile Lys His Val Cys Arg
            1060             1065             1070
Arg Ala Ala Val Ala Leu Gly Arg Lys Arg Ala Val Phe Pro Asp Asp
            1075             1080             1085
Met Pro Thr Leu Ser Ala Leu Pro Trp Glu Glu Arg Glu Lys Ile Leu
        1090             1095             1100
Ser Ser Met Gly Asn Asp Asp Lys Ser Ser Ile Ala Gly Ser Glu Asp
1105             1110             1115             1120
Ala Glu Pro Leu Ala Pro Pro Ile Lys Pro Ile Lys Pro Val Thr Arg
            1125             1130             1135
Asn Lys Ala Pro Gln Glu Pro Val Lys Lys Gly Arg Arg Ser Arg
            1140             1145             1150
Arg Cys Gly Gln Cys Pro Gly Cys Gln Val Pro Glu Asp Cys Gly Val
            1155             1160             1165
Cys Thr Asn Cys Leu Asp Lys Pro Lys Phe Gly Gly Arg Asn Ile Lys
        1170             1175             1180
Lys Gln Cys Cys Lys Met Arg Lys Cys Gln Asn Leu Gln Trp Met Pro
1185             1190             1195             1200
Ser Lys Ala Tyr Leu Gln Lys Gln Ala Lys Ala Val Lys Lys Lys Glu
                1205             1210             1215
Lys Lys Ser Lys Thr Ser Glu Lys Asp Ser Lys Glu Ser Ser Val
            1220             1225             1230
Val Lys Asn Val Val Asp Ser Ser Gln Lys Pro Thr Pro Ser Ala Arg
            1235             1240             1245
Glu Asp Pro Ala Pro Lys Lys Ser Ser Glu Pro Pro Arg Lys
        1250             1255             1260
Pro Val Glu Glu Lys Ser Glu Glu Gly Asn Val Ser Ala Pro Gly Pro
1265             1270             1275             1280
Glu Ser Lys Gln Ala Thr Thr Pro Ala Ser Arg Lys Ser Ser Lys Gln
                1285             1290             1295
Val Ser Gln Pro Ala Leu Val Ile Pro Pro Gln Pro Thr Thr Gly
            1300             1305             1310
Pro Pro Arg Lys Glu Val Pro Lys Thr Thr Pro Ser Glu Pro Lys Lys
            1315             1320             1325
```

```
Lys Gln Pro Pro Pro Glu Ser Gly Pro Gln Ser Lys Gln Lys
    1330            1335            1340

Lys Val Ala Pro Arg Pro Ser Ile Pro Val Lys Gln Lys Pro Lys Glu
1345            1350            1355            1360

Lys Glu Lys Pro Pro Val Asn Lys Gln Glu Asn Ala Gly Thr Leu
        1365            1370            1375

Asn Ile Leu Ser Thr Leu Ser Asn Gly Asn Ser Ser Lys Gln Lys Ile
            1380            1385            1390

Pro Ala Asp Gly Val His Arg Ile Arg Val Asp Phe Lys Glu Asp Cys
        1395            1400            1405

Glu Ala Glu Asn Val Trp Glu Met Gly Gly Leu Gly Ile Leu Thr Ser
    1410            1415            1420

Val Pro Ile Thr Pro Arg Val Val Cys Phe Leu Cys Ala Ser Ser Gly
1425            1430            1435            1440

His Val Glu Phe Val Tyr Cys Gln Val Cys Cys Glu Pro Phe His Lys
            1445            1450            1455

Phe Cys Leu Glu Glu Asn Glu Arg Pro Leu Glu Asp Gln Leu Glu Asn
        1460            1465            1470

Trp Cys Cys Arg Arg Cys Lys Phe Cys His Val Cys Gly Arg Gln His
        1475            1480            1485

Gln Ala Thr Lys Gln Leu Leu Glu Cys Asn Lys Cys Arg Asn Ser Tyr
    1490            1495            1500

His Pro Glu Cys Leu Gly Pro Asn Tyr Pro Thr Lys Pro Thr Lys Lys
1505            1510            1515            1520

Lys Lys Val Trp Ile Cys Thr Lys Cys Val Arg Cys Lys Ser Cys Gly
            1525            1530            1535

Ser Thr Thr Pro Gly Lys Gly Trp Asp Ala Gln Trp Ser His Asp Phe
        1540            1545            1550

Ser Leu Cys His Asp Cys Ala Lys Leu Phe Ala Lys Gly Asn Phe Cys
        1555            1560            1565

Pro Leu Cys Asp Lys Cys Tyr Asp Asp Asp Tyr Glu Ser Lys Met
    1570            1575            1580

Met Gln Cys Gly Lys Cys Asp Arg Trp Val His Ser Lys Cys Glu Asn
1585            1590            1595            1600

Leu Ser Asp Glu Met Tyr Glu Ile Leu Ser Asn Leu Pro Glu Ser Val
            1605            1610            1615

Ala Tyr Thr Cys Val Asn Cys Thr Glu Arg His Pro Ala Glu Trp Arg
        1620            1625            1630

Leu Ala Leu Glu Lys Glu Leu Gln Ile Ser Leu Lys Gln Val Leu Thr
        1635            1640            1645

Ala Leu Leu Asn Ser Arg Thr Thr Ser His Leu Leu Arg Tyr Arg Gln
    1650            1655            1660

Ala Ala Lys Pro Pro Asp Leu Asn Pro Glu Thr Glu Glu Ser Ile Pro
1665            1670            1675            1680

Ser Arg Ser Ser Pro Glu Gly Pro Asp Pro Pro Val Leu Thr Glu Val
            1685            1690            1695

Ser Lys Gln Asp Asp Gln Gln Pro Leu Asp Leu Glu Gly Val Lys Arg
        1700            1705            1710

Lys Met Asp Gln Gly Asn Tyr Thr Ser Val Leu Glu Phe Ser Asp Asp
        1715            1720            1725

Ile Val Lys Ile Ile Gln Ala Ala Ile Asn Ser Asp Gly Gly Gln Pro
    1730            1735            1740
```

-continued

```
Glu Ile Lys Lys Ala Asn Ser Met Val Lys Ser Phe Ile Arg Gln
1745                1750                1755                1760

Met Glu Arg Val Phe Pro Trp Phe Ser Val Lys Lys Ser Arg Phe Trp
        1765                1770                1775

Glu Pro Asn Lys Val Ser Ser Asn Ser Gly Met Leu Pro Asn Ala Val
            1780                1785                1790

Leu Pro Pro Ser Leu Asp His Asn Tyr Ala Gln Trp Gln Glu Arg Glu
        1795                1800                1805

Glu Asn Ser His Thr Glu Gln Pro Pro Leu Met Lys Lys Ile Ile Pro
    1810                1815                1820

Ala Pro Lys Pro Lys Gly Pro Gly Glu Pro Asp Ser Pro Thr Pro Leu
1825                1830                1835                1840

His Pro Pro Thr Pro Pro Ile Leu Ser Thr Asp Arg Ser Arg Glu Asp
            1845                1850                1855

Ser Pro Glu Leu Asn Pro Pro Gly Ile Glu Asp Asn Arg Gln Cys
        1860                1865                1870

Ala Leu Cys Leu Thr Tyr Gly Asp Asp Ser Ala Asn Asp Ala Gly Arg
            1875                1880                1885

Leu Leu Tyr Ile Gly Gln Asn Glu Trp Thr His Val Asn Cys Ala Leu
        1890                1895                1900

Trp Ser Ala Glu Val Phe Glu Asp Asp Gly Ser Leu Lys Asn Val
1905                1910                1915                1920

His Met Ala Val Ile Arg Gly Lys Gln Leu Arg Cys Glu Phe Cys Gln
            1925                1930                1935

Lys Pro Gly Ala Thr Val Gly Cys Cys Leu Thr Ser Cys Thr Ser Asn
            1940                1945                1950

Tyr His Phe Met Cys Ser Arg Ala Lys Asn Cys Val Phe Leu Asp Asp
        1955                1960                1965

Lys Lys Val Tyr Cys Gln Arg His Arg Asp Leu Ile Lys Gly Glu Val
        1970                1975                1980

Val Pro Glu Asn Gly Phe Glu Val Phe Arg Arg Val Phe Val Asp Phe
1985                1990                1995                2000

Glu Gly Ile Ser Leu Arg Arg Lys Phe Leu Asn Gly Leu Glu Pro Glu
        2005                2010                2015

Asn Ile His Met Met Ile Gly Ser Met Thr Ile Asp Cys Leu Gly Ile
        2020                2025                2030

Leu Asn Asp Leu Ser Asp Cys Glu Asp Lys Leu Phe Pro Ile Gly Tyr
        2035                2040                2045

Gln Cys Ser Arg Val Tyr Trp Ser Thr Thr Asp Ala Arg Lys Arg Cys
    2050                2055                2060

Val Tyr Thr Cys Lys Ile Val Glu Cys Arg Pro Val Val Glu Pro
2065                2070                2075                2080

Asp Ile Asn Ser Thr Val Glu His Asp Glu Asn Arg Thr Ile Ala His
        2085                2090                2095

Ser Pro Thr Ser Phe Thr Glu Ser Ser Lys Glu Ser Gln Asn Thr
            2100                2105                2110

Ala Glu Ile Ile Ser Pro Pro Ser Pro Asp Arg Pro Pro His Ser Gln
        2115                2120                2125

Thr Ser Gly Ser Cys Tyr Tyr His Val Ile Ser Lys Val Pro Arg Ile
        2130                2135                2140

Arg Thr Pro Ser Tyr Ser Pro Thr Gln Arg Ser Pro Gly Cys Arg Pro
2145                2150                2155                2160

Leu Pro Ser Ala Gly Ser Pro Thr Pro Thr Thr His Glu Ile Val Thr
```

-continued

```
                2165                2170                2175

Val Gly Asp Pro Leu Ser Ser Gly Leu Arg Ser Ile Gly Ser Arg
                2180                2185                2190

Arg His Ser Thr Ser Ser Leu Ser Pro Gln Arg Ser Lys Leu Arg Ile
            2195                2200                2205

Met Ser Pro Met Arg Thr Gly Asn Thr Tyr Ser Arg Asn Asn Val Ser
        2210                2215                2220

Ser Val Ser Thr Thr Gly Thr Ala Thr Asp Leu Glu Ser Ser Ala Lys
2225                2230                2235                2240

Val Val Asp His Val Leu Gly Pro Leu Asn Ser Ser Thr Ser Leu Gly
            2245                2250                2255

Gln Asn Thr Ser Thr Ser Ser Asn Leu Gln Arg Thr Val Val Thr Val
        2260                2265                2270

Gly Asn Lys Asn Ser His Leu Asp Gly Ser Ser Ser Glu Met Lys
    2275                2280                2285

Gln Ser Ser Ala Ser Asp Leu Val Ser Lys Ser Ser Ser Leu Lys Gly
    2290                2295                2300

Glu Lys Thr Lys Val Leu Ser Ser Lys Ser Ser Glu Gly Ser Ala His
2305                2310                2315                2320

Asn Val Ala Tyr Pro Gly Ile Pro Lys Leu Ala Pro Gln Val His Asn
            2325                2330                2335

Thr Thr Ser Arg Glu Leu Asn Val Ser Lys Ile Gly Ser Phe Ala Glu
        2340                2345                2350

Pro Ser Ser Val Ser Phe Ser Ser Lys Glu Ala Leu Ser Phe Pro His
    2355                2360                2365

Leu His Leu Arg Gly Gln Arg Asn Asp Arg Asp Gln His Thr Asp Ser
    2370                2375                2380

Thr Gln Ser Ala Asn Ser Ser Pro Asp Glu Asp Thr Glu Val Lys Thr
2385                2390                2395                2400

Leu Lys Leu Ser Gly Met Ser Asn Arg Ser Ser Ile Ile Asn Glu His
            2405                2410                2415

Met Gly Ser Ser Ser Arg Asp Arg Arg Gln Lys Gly Lys Lys Ser Cys
            2420                2425                2430

Lys Glu Thr Phe Lys Glu Lys His Ser Ser Lys Ser Phe Leu Glu Pro
        2435                2440                2445

Gly Gln Val Thr Thr Gly Glu Glu Gly Asn Leu Lys Pro Glu Phe Met
    2450                2455                2460

Asp Glu Val Leu Thr Pro Glu Tyr Met Gly Gln Arg Pro Cys Asn Asn
2465                2470                2475                2480

Val Ser Ser Asp Lys Ile Gly Asp Lys Gly Leu Ser Met Pro Gly Val
            2485                2490                2495

Pro Lys Ala Pro Pro Met Gln Val Glu Gly Ser Ala Lys Glu Leu Gln
        2500                2505                2510

Ala Pro Arg Lys Arg Thr Val Lys Val Thr Leu Thr Pro Leu Lys Met
    2515                2520                2525

Glu Asn Glu Ser Gln Ser Lys Asn Ala Leu Lys Glu Ser Ser Pro Ala
    2530                2535                2540

Ser Pro Leu Gln Ile Glu Ser Thr Ser Pro Thr Glu Pro Ile Ser Ala
2545                2550                2555                2560

Ser Glu Asn Pro Gly Asp Gly Pro Val Ala Gln Pro Ser Pro Asn Asn
            2565                2570                2575

Thr Ser Cys Gln Asp Ser Gln Ser Asn Asn Tyr Gln Asn Leu Pro Val
            2580                2585                2590
```

-continued

```
Gln Asp Arg Asn Leu Met Leu Pro Asp Gly Pro Lys Pro Gln Glu Asp
        2595                2600                2605

Gly Ser Phe Lys Arg Arg Tyr Pro Arg Ser Ala Arg Ala Arg Ser
2610                2615                2620

Asn Met Phe Phe Gly Leu Thr Pro Leu Tyr Gly Val Arg Ser Tyr Gly
2625                2630                2635                2640

Glu Glu Asp Ile Pro Phe Tyr Ser Ser Ser Thr Gly Lys Lys Arg Gly
                2645                2650                2655

Lys Arg Ser Ala Glu Gly Gln Val Asp Gly Ala Asp Asp Leu Ser Thr
        2660                2665                2670

Ser Asp Glu Asp Asp Leu Tyr Tyr Tyr Asn Phe Thr Arg Thr Val Ile
        2675                2680                2685

Ser Ser Gly Gly Glu Glu Arg Leu Ala Ser His Asn Leu Phe Arg Glu
        2690                2695                2700

Glu Glu Gln Cys Asp Leu Pro Lys Ile Ser Gln Leu Asp Gly Val Asp
2705                2710                2715                2720

Asp Gly Thr Glu Ser Asp Thr Ser Val Thr Ala Thr Thr Arg Lys Ser
                2725                2730                2735

Ser Gln Ile Pro Lys Arg Asn Gly Lys Glu Asn Gly Thr Glu Asn Leu
        2740                2745                2750

Lys Ile Asp Arg Pro Glu Asp Ala Gly Glu Lys Glu His Val Thr Lys
        2755                2760                2765

Ser Ser Val Gly His Lys Asn Glu Pro Lys Met Asp Asn Cys His Ser
        2770                2775                2780

Val Ser Arg Val Lys Thr Gln Gly Gln Asp Ser Leu Glu Ala Gln Leu
2785                2790                2795                2800

Ser Ser Leu Glu Ser Ser Arg Arg Val His Thr Ser Thr Pro Ser Asp
                2805                2810                2815

Lys Asn Leu Leu Asp Thr Tyr Asn Thr Glu Leu Leu Lys Ser Asp Ser
        2820                2825                2830

Asp Asn Asn Asn Ser Asp Asp Cys Gly Asn Ile Leu Pro Ser Asp Ile
        2835                2840                2845

Met Asp Phe Val Leu Lys Asn Thr Pro Ser Met Gln Ala Leu Gly Glu
        2850                2855                2860

Ser Pro Glu Ser Ser Ser Ser Glu Leu Leu Asn Leu Gly Glu Gly Leu
2865                2870                2875                2880

Gly Leu Asp Ser Asn Arg Glu Lys Asp Met Gly Leu Phe Glu Val Phe
                2885                2890                2895

Ser Gln Gln Leu Pro Thr Thr Glu Pro Val Asp Ser Ser Val Ser Ser
        2900                2905                2910

Ser Ile Ser Ala Glu Glu Gln Phe Glu Leu Pro Leu Glu Leu Pro Ser
        2915                2920                2925

Asp Leu Ser Val Leu Thr Thr Arg Ser Pro Thr Val Pro Ser Gln Asn
        2930                2935                2940

Pro Ser Arg Leu Ala Val Ile Ser Asp Ser Gly Glu Lys Arg Val Thr
2945                2950                2955                2960

Ile Thr Glu Lys Ser Val Ala Ser Ser Glu Ser Asp Pro Ala Leu Leu
                2965                2970                2975

Ser Pro Gly Val Asp Pro Thr Pro Glu Gly His Met Thr Pro Asp His
        2980                2985                2990

Phe Ile Gln Gly His Met Asp Ala Asp His Ile Ser Ser Pro Pro Cys
        2995                3000                3005
```

-continued

Gly Ser Val Glu Gln Gly His Gly Asn Asn Gln Asp Leu Thr Arg Asn
    3010                3015                3020

Ser Ser Thr Pro Gly Leu Gln Val Pro Val Ser Pro Thr Val Pro Ile
3025                3030                3035                3040

Gln Asn Gln Lys Tyr Val Pro Asn Ser Thr Asp Ser Pro Gly Pro Ser
                3045                3050                3055

Gln Ile Ser Asn Ala Ala Val Gln Thr Thr Pro Pro His Leu Lys Pro
            3060                3065                3070

Ala Thr Glu Lys Leu Ile Val Val Asn Gln Asn Met Gln Pro Leu Tyr
        3075                3080                3085

Val Leu Gln Thr Leu Pro Asn Gly Val Thr Gln Lys Ile Gln Leu Thr
    3090                3095                3100

Ser Ser Val Ser Ser Thr Pro Ser Val Met Glu Thr Asn Thr Ser Val
3105                3110                3115                3120

Leu Gly Pro Met Gly Gly Gly Leu Thr Leu Thr Thr Gly Leu Asn Pro
                3125                3130                3135

Ser Leu Pro Thr Ser Gln Ser Leu Phe Pro Ser Ala Ser Lys Gly Leu
            3140                3145                3150

Leu Pro Met Ser His His Gln His Leu His Ser Phe Pro Ala Ala Thr
        3155                3160                3165

Gln Ser Ser Phe Pro Pro Asn Ile Ser Asn Pro Pro Ser Gly Leu Leu
    3170                3175                3180

Ile Gly Val Gln Pro Pro Pro Asp Pro Gln Leu Leu Val Ser Glu Ser
3185                3190                3195                3200

Ser Gln Arg Thr Asp Leu Ser Thr Thr Val Ala Thr Pro Ser Ser Gly
                3205                3210                3215

Leu Lys Lys Arg Pro Ile Ser Arg Leu Gln Thr Arg Lys Asn Lys Lys
            3220                3225                3230

Leu Ala Pro Ser Ser Thr Pro Ser Asn Ile Ala Pro Ser Asp Val Val
        3235                3240                3245

Ser Asn Met Thr Leu Ile Asn Phe Thr Pro Ser Gln Leu Pro Asn His
    3250                3255                3260

Pro Ser Leu Leu Asp Leu Gly Ser Leu Asn Thr Ser Ser His Arg Thr
3265                3270                3275                3280

Val Pro Asn Ile Ile Lys Arg Ser Lys Ser Ser Ile Met Tyr Phe Glu
                3285                3290                3295

Pro Ala Pro Leu Leu Pro Gln Ser Val Gly Gly Thr Ala Ala Thr Ala
            3300                3305                3310

Ala Gly Thr Ser Thr Ile Ser Gln Asp Thr Ser His Leu Thr Ser Gly
        3315                3320                3325

Ser Val Ser Gly Leu Ala Ser Ser Ser Ser Val Leu Asn Val Val Ser
    3330                3335                3340

Met Gln Thr Thr Thr Thr Pro Thr Ser Ser Ala Ser Val Pro Gly His
3345                3350                3355                3360

Val Thr Leu Thr Asn Pro Arg Leu Leu Gly Thr Pro Asp Ile Gly Ser
                3365                3370                3375

Ile Ser Asn Leu Leu Ile Lys Ala Ser Gln Gln Ser Leu Gly Ile Gln
            3380                3385                3390

Asp Gln Pro Val Ala Leu Pro Pro Ser Ser Gly Met Phe Pro Gln Leu
        3395                3400                3405

Gly Thr Ser Gln Thr Pro Ser Thr Ala Ala Ile Thr Ala Ala Ser Ser
    3410                3415                3420

Ile Cys Val Leu Pro Ser Thr Gln Thr Thr Gly Ile Thr Ala Ala Ser

-continued

```
3425                3430                3435                3440
Pro Ser Gly Glu Ala Asp Glu His Tyr Gln Leu Gln His Val Asn Gln
                3445                3450                3455
Leu Leu Ala Ser Lys Thr Gly Ile His Ser Ser Gln Arg Asp Leu Asp
                3460                3465                3470
Ser Ala Ser Gly Pro Gln Val Ser Asn Phe Thr Gln Thr Val Asp Ala
                3475                3480                3485
Pro Asn Ser Met Gly Leu Glu Gln Asn Lys Ala Leu Ser Ser Ala Val
                3490                3495                3500
Gln Ala Ser Pro Thr Ser Pro Gly Gly Ser Pro Ser Ser Pro Ser Ser
3505                3510                3515                3520
Gly Gln Arg Ser Ala Ser Pro Ser Val Pro Gly Pro Thr Lys Pro Lys
                3525                3530                3535
Pro Lys Thr Lys Arg Phe Gln Leu Pro Leu Asp Lys Gly Asn Gly Lys
                3540                3545                3550
Lys His Lys Val Ser His Leu Arg Thr Ser Ser Ser Glu Ala His Ile
                3555                3560                3565
Pro Asp Gln Glu Thr Thr Ser Leu Thr Ser Gly Thr Gly Thr Pro Gly
                3570                3575                3580
Ala Glu Ala Glu Gln Gln Asp Thr Ala Ser Val Glu Gln Ser Ser Gln
3585                3590                3595                3600
Lys Glu Cys Gly Gln Pro Ala Gly Gln Val Ala Val Leu Pro Glu Val
                3605                3610                3615
Gln Val Thr Gln Asn Pro Ala Asn Glu Gln Glu Ser Ala Glu Pro Lys
                3620                3625                3630
Thr Val Glu Glu Glu Ser Asn Phe Ser Ser Pro Leu Met Leu Trp
                3635                3640                3645
Leu Gln Gln Glu Gln Lys Arg Lys Glu Ser Ile Thr Glu Lys Lys Pro
3650                3655                3660
Lys Lys Gly Leu Val Phe Glu Ile Ser Ser Asp Asp Gly Phe Gln Ile
3665                3670                3675                3680
Cys Ala Glu Ser Ile Glu Asp Ala Trp Lys Ser Leu Thr Asp Lys Val
                3685                3690                3695
Gln Glu Ala Arg Ser Asn Ala Arg Leu Lys Gln Leu Ser Phe Ala Gly
                3700                3705                3710
Val Asn Gly Leu Arg Met Leu Gly Ile Leu His Asp Ala Val Val Phe
                3715                3720                3725
Leu Ile Glu Gln Leu Ser Gly Ala Lys His Cys Arg Asn Tyr Lys Phe
                3730                3735                3740
Arg Phe His Lys Pro Glu Glu Ala Asn Glu Pro Pro Leu Asn Pro His
3745                3750                3755                3760
Gly Ser Ala Arg Ala Glu Val His Leu Arg Lys Ser Ala Phe Asp Met
                3765                3770                3775
Phe Asn Phe Leu Ala Ser Lys His Arg Gln Pro Pro Glu Tyr Asn Pro
                3780                3785                3790
Asn Asp Glu Glu Glu Glu Val Gln Leu Lys Ser Ala Arg Arg Ala
                3795                3800                3805
Thr Ser Met Asp Leu Pro Met Pro Met Arg Phe Arg His Leu Lys Lys
                3810                3815                3820
Thr Ser Lys Glu Ala Val Gly Val Tyr Arg Ser Pro Ile His Gly Arg
3825                3830                3835                3840
Gly Leu Phe Cys Lys Arg Asn Ile Asp Ala Gly Glu Met Val Ile Glu
                3845                3850                3855
```

```
Tyr Ala Gly Asn Val Ile Arg Ser Ile Gln Thr Asp Lys Arg Glu Lys
            3860                3865                3870

Tyr Tyr Asp Ser Lys Gly Ile Gly Cys Tyr Met Phe Arg Ile Asp Asp
            3875                3880                3885

Ser Glu Val Val Asp Ala Thr Met His Gly Asn Arg Ala Arg Phe Ile
            3890                3895                3900

Asn His Ser Cys Glu Pro Asn Cys Tyr Ser Arg Val Ile Asn Ile Asp
3905                3910                3915                3920

Gly Gln Lys His Ile Val Ile Phe Ala Met Arg Lys Ile Tyr Arg Gly
            3925                3930                3935

Glu Glu Leu Thr Tyr Asp Tyr Lys Phe Pro Ile Glu Asp Ala Ser Asn
            3940                3945                3950

Lys Leu Pro Cys Asn Cys Gly Ala Lys Lys Cys Arg Lys Phe Leu Asn
            3955                3960                3965

Glx (2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: both
        (D) TOPOLOGY: both (ii) MOLECULE TYPE: DNA (genomic)

(ix) FEATURE:
        (A) NAME/KEY: CDS
        (B) LOCATION: 1..51
        (D) OTHER INFORMATION: /product= "Genomic nucleotide
            sequence encoding ORF1"

(xi) SEQUENCE DESCRIPTION: SEQ ID NO:6:

TTC TTT AAC AGA CAA TGC ATC AAT TGC TGG CTC AGA AGA TGC ATG ACC      48
Phe Phe Asn Arg Gln Cys Ile Asn Cys Trp Leu Arg Arg Cys Met Thr
 1               5                  10                  15

AGC                                                                  51
Ser (2) INFORMATION FOR SEQ ID NO:7:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:7:

Phe Phe Asn Arg Gln Cys Ile Asn Cys Trp Leu Arg Arg Cys Met Thr
 1               5                  10                  15

Ser (2) INFORMATION FOR SEQ ID NO:8:

(i) SEQUENCE CHARACTERISTICS:
        (A) LENGTH: 17 amino acids
        (B) TYPE: amino acid
        (D) TOPOLOGY: unknown (ii) MOLECULE TYPE: protein (v) FRAGMENT TYPE: internal
```

```
    (xi) SEQUENCE DESCRIPTION: SEQ ID NO:8:

Phe Tyr Lys Asp Arg Cys Thr Ala Cys Trp Leu Lys Lys Cys Met Ile
1               5                   10                  15

Ser (2) INFORMATION FOR SEQ ID NO:9:

(i) SEQUENCE CHARACTERISTICS:
        (A) LENGTH: 24 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:9:

Asp Glu Met Tyr Glu Ile Leu Ser Asn Leu Pro Glu Ser Val Ala Tyr
1               5                   10                  15

Thr Cys Val Asn Cys Thr Glu Arg
            20

(2) INFORMATION FOR SEQ ID NO:10:

(i) SEQUENCE CHARACTERISTICS:
        (A) LENGTH: 24 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:10:

Asp Glu Gln Tyr Asn Leu Leu Ser Thr Leu Pro Glu Ser Ile Glu Phe
1               5                   10                  15

Ile Cys Lys Lys Cys Ala Arg Arg
            20

(2) INFORMATION FOR SEQ ID NO:11:

(i) SEQUENCE CHARACTERISTICS:
        (A) LENGTH: 77 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:11:

Asp Phe Ser Leu Cys His Asp Cys Ala Lys Leu Phe Ala Lys Gly Asn
1               5                   10                  15

Phe Cys Pro Leu Cys Asp Lys Cys Tyr Asp Asp Asp Tyr Glu Ser
            20                  25                  30

Lys Met Met Gln Cys Gly Lys Cys Asp Arg Trp Val His Ser Lys Cys
            35                  40                      45

Glu Asn Leu Ser Asp Glu Met Tyr Glu Ile Leu Ser Asn Leu Pro Glu
        50                  55                      60

Ser Val Ala Tyr Thr Cys Val Asn Cys Thr Glu Arg His
65                  70                  75

(2) INFORMATION FOR SEQ ID NO:12:
```

```
        (i) SEQUENCE CHARACTERISTICS:
            (A) LENGTH: 77 amino acids
            (B) TYPE: amino acid
            (D) TOPOLOGY: unknown (ii) MOLECULE TYPE: protein (v) FRAGMENT TYPE: internal (xi) SEQUENCE DESCRIPTION: SEQ ID NO:12:

Asn Leu Pro Met Cys Thr Gly Cys Phe Lys Leu Arg Lys Lys Gly Asn
1               5                   10                  15

Phe Cys Pro Ile Cys Gln Arg Cys Tyr Asp Asp Asn Asp Phe Asp Leu
                20                  25                  30

Lys Met Met Glu Cys Gly Asp Cys Gly Gln Trp Val His Ser Lys Cys
            35                  40                  45

Glu Gly Leu Ser Asp Glu Gln Tyr Asn Leu Leu Ser Thr Leu Pro Glu
        50                  55                  60

Ser Ile Glu Phe Ile Cys Lys Lys Cys Ala Arg Arg Asn
65                  70                  75
```

NUCLEIC ACIDS ENCODING HUMAN TRITHORAX PROTEIN

RELATED INVENTIONS

This application is a continuation-in-part of U.S. Ser. No. 07/954,112, filed Sep. 30, 1992, now abandoned.

ACKNOWLEDGEMENT

This invention was made with Government support under Grant No. HG00202, awarded by the National Institutes of Health and Grant No. DE-FG03-88ER60694/A6, awarded by the Department of Energy. The Government may have certain rights in the invention.

FIELD OF THE INVENTION

This invention relates to analytical and diagnostic methods, as well as novel polynucleotide sequences and peptides encoded thereby. In a particular aspect, this invention relates to methods for identifying the existence of specific chromosomal aberrations in the genome of a host subject. In another aspect, this invention relates to methods for diagnosing actual or nascent disease states employing the information obtained, applying the invention technique(s) for the determination of the presence of chromosomal aberrations.

BACKGROUND OF THE INVENTION

Specific chromosome translocations are characteristic of some leukaemias and solid tumors, and may lead to malignant transformation through the activation or aberrant expression of breakpoint-associated genes [Berger et al., Leukemia Res. Vol. 6:17–26 (1982)]. For example, rearrangements involving human chromosome region 11 q23 are observed in acute leukaemias, especially t(4;11), t(1;11), and t(11;19) in acute lymphoid leukaemias (ALL) [see, for example, Mazo et al., Proc. Natl. Acad. Sci. USA Vol. 87:2112–2116 (1990)]; and t(1;11) t(2;11), t(6;11), t(9;11), t(10;11), t(11;17) and t(X;11) in acute myeloid leukaemia (AML) [see, for example, Sait et al., Cancer Genet. Cytogenet. Vol. 24:181–183 (1987), Feder et al., Cancer Genet. Cytogenet. Vol. 15:143–150), Derre et al., Gene Chromosom. Cancer Vol. 2:341–344 (1990, Hagemeijer et al., Cancer Genet. Cytogenet. Vol. 5:95–105 (1982), and Pui et al., Blood Vol. 69:1289–1293 (1987)].

The frequency of 11 q23 abnormalities is particularly high in leukaemia occurring in infants, accounting for more than 75% of acute leukaemias in those under 12 months of age [see, for example, Abe et al., Cancer Genet. Cytogenet. Vol. 9:139–144 (1983), Chuu et al., Am. J. Hematol. Vol. 34:246–251 (1990), and Gibbons et al., Br. J. Hematol. Vol. 74:264–269 (1990)]. Leukaemia cells isolated from ALLs with the t(4;11) translocation typically exhibit monocytic as well as lymphocytic characteristics, leading to speculation that the gene or genes located at the translocation breakpoint might affect development of an early lymphoid/myeloid precursor stem cell [see Rowley et al., Proc. Natl. Acad. Sci. USA Vol. 87:9358–9362 (1990)].

Previous studies have localized the t(4;11) breakpoint and the t(9;11) breakpoint associated with acute monoblastic (M4-AML) or myelomonocytic (M5-AMML) leukaemias to the same 5.8 kb region of chromosome 11 q23 [see Cimino et al., Cancer Research Vol. 51:6712–6714 (1991)]. Recently, other studies have identified large 11 to 12 kb transcripts arising from the region of the t(4;11) (q21:q23) translocation [see, for example, Ziemin-van der poel et al., Proc. Natl. Acad. Sci. USA Vol. 88:10735–10739 (1991), and Cimino et al., Cancer Research Vol. 52:3811–3813 (1992)].

Accordingly, since consistent chromosome translocations have been associated with a number of human malignancies (including leukaemias, lymphomas and solid tumors), and such translocations may be intimately involved in the molecular pathogenesis of the associated disorders, the development of rapid and effective methods to analyze for the presence of chromosomal aberrations related to such disease states (e.g., translocations involving a chromosomal site of interest) would provide a useful aid in the diagnosis of actual or nascent disease states.

BRIEF DESCRIPTION OF THE INVENTION

In order to isolate the loci of chromosome 11 involved in acute lymphoid leukaemias (ALL) and acute myeloid leukaemias (AML), as well as other leukaemia-associated breakpoints believed to be present on chromosome 11, extensive physical mapping of chromosome 11 q23 was carried out by the isolation of yeast artificial chromosomes. In the course of construction of a physical map of human chromosome region 11 q23, the region containing the t(4;11) and t(9;11) translocation breakpoint was cloned, and genes whose expression is affected by chromosome rearrangement were identified. Presented herein is a physical map and the DNA sequence of the translocation breakpoint, as well as the identity of the sequences in the immediate proximity of this breakpoint.

The DNA sequence of the breakpoint region shows that one of the transcripts of the DNA isolated in accordance with the present invention is interrupted as a result of translocation, and corresponds to a human gene homologous to the *Drosophila trithorax* (trx) gene product.

BRIEF DESCRIPTION OF THE FIGURES

FIG. 1 shows a physical map of chromosome 11 q,23 in the region of the t(4;11) and t(9;11) leukaemia-associated breakpoints.

FIG. 2 characterizes the DNA sequence where the t(4;11) translocation breakpoint occurs, plus surrounding sequence.

FIG. 2A is a diagram of the structure of this region showing locations of repetitive sequences as well as putative exons of a gene spanning the breakpoint. ■ indicates the location of Alu repetitive elements; □ indicates the location of sequence homologous to a portion of the LINE-1 repetitive element; ※ indicates open reading frames representing putative exons (R=EcoRl, X=XbaI). The location of the t(4;11) breakpoint (as determined by Southern gel analysis on DNA from the RS4;11 cell line) is indicated in the figure. A substantial portion (~3 kb) of cDNA encoding the human *trithorax* gene (htrx) has been deposited in Genbank as accession number LO1986. The 5' portion of this sequence is reproduced below as SEQ ID NO: 2, and the 3' portion of this sequence is reproduced below as SEQ ID NO:3. Additional sequence linking SEQ ID NO:2 and SEQ ID NO:3 is presented in SEQ ID NO:4, which also includes sequence information extending further upstream of the 5' portion set forth in SEQ ID NO:2, and further downstream of the 3' portion set forth in SEQ ID NO:3. Thus, SEQ ID NO:4 provides a substantially complete sequence of htrx-encoding cDNA.

FIG. 2B shows an analysis of open reading frames on either side of the breakpoint, demonstrating the occurrence of sequence similarity (and presumed homology) to the *Drosophila trithorax* gene product. ORF1 (see SEQ ID NOS: 6 and 7) and ORF2 (see amino acid residues 1603 to 1626 of SEQ ID NO: 5) represent sequences of exons flanking the translocation breakpoint at the centromeric and telomeric sides. ORF3 (see amino acid residues 1551, to 1627 of SEQ ID NO: 5) represents the open reading frame derived from a cDNA clone corresponding to ORF2. | indicates a perfect match and+indicates a conservative substitution. Cysteine residues within the *Drosophila trx* zinc finger domains 2 and 6a are boxed.

FIG. 3 provides a genomic map of the breakpoint region on chromosome 11 q23. The restriction sites shown are R, EcoRI; B, BamHI; H, HindIII; X, XbaI. The exon/intron structure for a partial cDNA (~3 kb) encoding htrxl is also shown in the figure (the 9 exons within this partial cDNA are boxed in black). The positions of the putative zinc fingers (numbers 3–8) are indicated on a schematical representation of the protein. The position of breakpoints in cell lines has been mapped accurately while the breaks in patients are clustered over 13 kb of genomic DNA shown by the shaded area on the diagram.

FIG. 4 provides further characterization of human trx. Thus, FIG. 4(A) illustrates the pattern of cysteine (C) and histidine (H) residues in the cysteine-rich regions of htrxl. The putative zinc finger structures are indicated by lines above the sequence; the numbers above each line refer to the Drosophila zinc fingers. The dotted lines indicate alternative zinc finger domains.

FIG. 4(B) denotes the putative zinc finger domains of htrxl protein, including an alignment of the human trx (bottom) to the proposed finger structures of the *Drosophila trx* zinc fingers (top). Drosophila domain numbers are given on the left; the last residue of each structure is given on the right. Amino acids that are identical between Drosophila and human are boxed in black; conservative changes are boxed.

DETAILED DESCRIPTION OF THE INVENTION

Figure 1A:
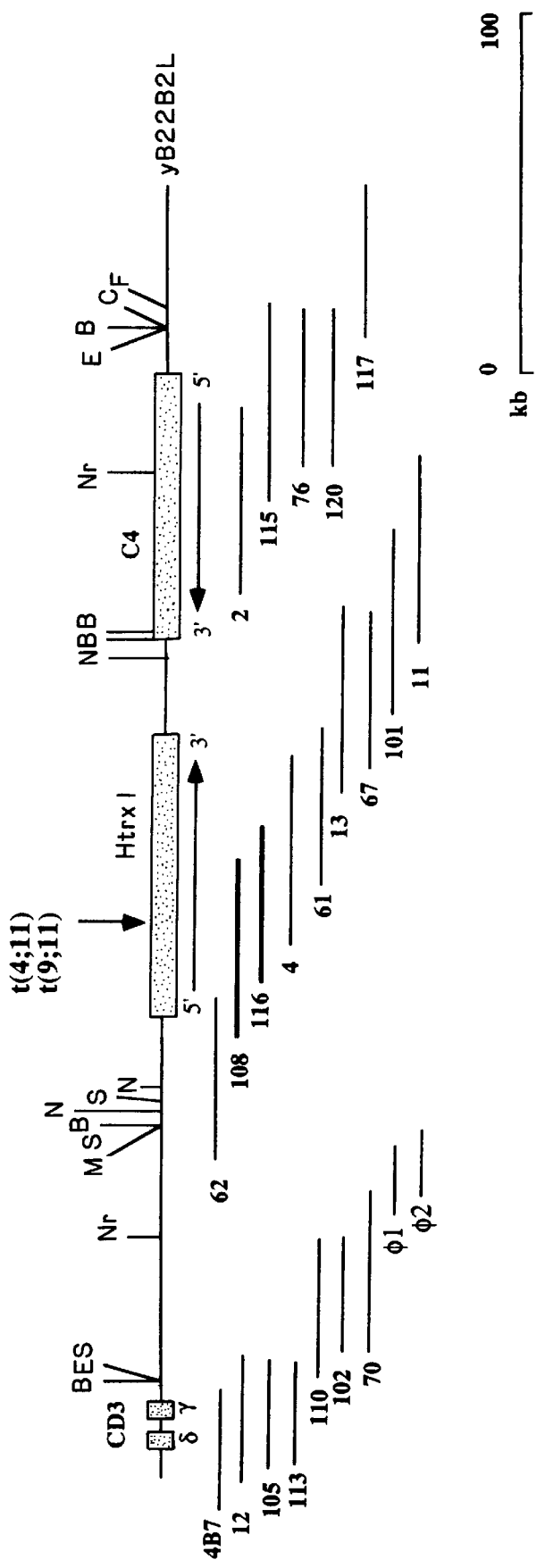
FIG. 1A shows YAC clone B22B2L. The locations of transcripts from this clone are indicated in the figure, as are restriction sites (B=BssHII; E=EagI; Nr=NruI; M=MluI; S=SacII; N=NotI; C=ClaI; and F=StiI). The location of the t(4;11) and t(9;11) breakpoints (as determined by pulsed field gel analysis), as well as the location of the CD3 γ and δ genes, are also indicated. The centromeric end of the YAC clone lies within the CD3 gene cluster (between the CD3 δ and ε genes; see Evans et al., Immunogenetics Vol. 28:365–373 (1988)).

In accordance with the present invention, there are provided isolated peptide(s) having the characteristics of human *trithorax* protein. Invention peptides are characterized by having a DNA binding domain comprising multiple zinc fingers and at least 40% amino acid identity with respect to the DNA binding domain of *Drosophila trithorax* protein and at least 70% conserved sequence with respect to the DNA binding domain of *Drosophila trithorax* protein, wherein said peptides are encoded by a gene located at chromosome 11 of the human genome at q23.

Preferred peptides of the present invention have substantially the same sequence as set forth in SEQ ID NO: 5.

In accordance with another embodiment of the present invention, there are provided nucleic acids encoding peptides as described above, or nucleic acids capable of hybridizing therewith under low stringency hybridization conditions. Preferred nucleic acids according to the present invention are DNA, with particularly preferred DNA having substantially the same sequence as set forth in SEQ ID NOS: 1, 2, 3 or 4, or DNA capable of hybridizing therewith under low stringency hybridization conditions.

Also contemplated by the present invention are splice variants, i.e., variant trx-encoding nucleic acids produced by differential processing of primary transcripts of genomic DNA, resulting in the production of more than one type of mRNA. cDNA derived from differentially processed genomic DNA will encode trx proteins that have regions of complete amino acid identity and regions lacking amino acid identity (or differing by the deletion of sequences in the splice variant relative to the "parental" sequence). Thus, the same genomic sequence can lead to the production of multiple, related mRNAs and proteins. Both the resulting mRNAs and proteins are referred to herein. as "splice variants."

In accordance with yet another embodiment of the present invention, there is provided antisense nucleic acid complementary to the above-described nucleic acids.

As employed herein, the phrase "*Drosophila trithorax* gene product" refers to a trans-acting regulator of the bithorax complex in Drosophila [see, for example, Mazo et al., in Proc. Natl. Acad. Sci. USA Vol. 87:2112–2116 (1990)]. The *Drosophila trithorax* gene product is an important regulatory protein which controls several derivative pathways. The *Drosophila trithorax* gene product is known to bind DNA at specific sites, and to regulate transcription of homeobox genes as well as the bithorax complex. The human homolog thereof, as described herein, is believed to have similarly important regulatory properties in humans. The peptide has several zinc finger domains characteristic of DNA binding proteins. The human trx protein is believed to be involved in varying stages of development, possibly by undergoing developmentally regulated alternate splicing, producing different gene products which exert different regulatory effects.

As employed herein, the phrase "conservative substitution" refers to the replacement of one amino acid residue with a different amino acid residue having similar chemical and physical properties. Thus, a conservative substitution refers, for example, to the replacement of one positively charged amino acid residue with another positively charged residue.

As employed herein, the phrase "isolated" refers to peptides which have been removed from their native environment, either by enrichment thereof from natural sources, by chemical synthesis, by recombinant production, and the like. Thus, the recombinant expression of human *trithorax* gene would produce an "isolated" peptide, since such expression would produce the peptide in a non-native environment. Similarly, substantial enrichment of the *trithorax* content of a cell extract would also provide an "isolated" peptide.

In accordance with still another embodiment of the present invention, there is provided a method for the treatment of a subject suffering from immunodeficiency, developmental abnormality, inherited disease, or cancer, said method comprising administering to said subject a therapeutically effective amount of the above-described peptide, or antagonists thereto.

In accordance with a still further embodiment of the present invention, there is provided a method for the treatment of a subject suffering from immunodeficiency states, developmental abnormalities, inherited diseases, or cancer, said method comprising administering to said subject an effective amount of the above-described antisense nucleic acid.

As employed herein, the phrase "therapeutically effective amount" refers to levels of peptide, nucleic acid or pharmaceutically active compound sufficient to provide circulating concentrations high enough to effect a modulation of the biological process involved in the immunodeficiency state, developmental abnormality, inherited disease, or cancer to be treated, without substantially compromising other biological processes. Such a concentration typically falls in the range of about 10 nM up to about 1 $\mu$M, with concentrations in the range of about 100 nM up to 500 nM being presently preferred.

Immunodeficiency states, developmental abnormalities, inherited diseases, or cancers contemplated for treatment in accordance with the present invention include such cancers as infantile acute lymphocytic leukemia, acute myelomonocytic leukemia, and the like.

In accordance with yet another embodiment of the present invention, there is provided a method for the diagnosis, in a subject, of immunodeficiency, developmental abnormality, inherited disease, or cancer associated with alterations (e.g., deletions, disruptions, rearrangements, and the like) of chromosome 11 at q23, said method comprising analyzing biological material obtained from said subject for evidence of a defect in the gene encoding human *trithorax* peptide.

Subjects for which the invention technique will find use include, broadly, any vertebrate species, e.g., fowl, fish, reptiles, amphibians, mammals and the like. Presently preferred subjects to be tested employing the invention technique are humans because of the ability to tailor treatment once the cause of an observed disease state is known with some certainty.

The invention diagnostic technique is capable of identifying the existence of a variety of chromosomal aberrations, e.g., deletions, inversions, duplications, translocations, the formation of ringed chromosomes, and the like.

In accordance with the present invention, a cell sample from a host subject is contacted with one or more probes constructed from chromosomal DNA derived from a subject of the same species as the subject being tested. The amount of detail provided by a given hybridization reaction is a function of how many probes are used for the hybridization reaction, and how much is known about each probe employed. For example, a single probe could be used, if such probe were diagnostic for a specific aberration of interest, e.g., translocation between chromosome 11 and chromosome 1, 2, 4, 6, 9, 10, 17, 22 or X. Such a probe would be derived from that portion of chromosome 11 and/or chromosome 1, 2, 4, 6, 9, 10, 17, 22 or X, where the Doss and/or gain of chromosomal DNA occurs upon translocation. Thus, upon hybridization, a different pattern of hybridization between probe and test DNA will be observed, relative to the pattern of hybridization obtained with normal DNA.

Alternatively, a cell sample from a subject suspected of containing a chromosomal aberration can be contacted with a panel of probes, wherein a typical "panel of probes" contains a sufficient number of probes so that, on average, for each chromosome, there are about 300 kilobases between probes. Panels can be a collection of probes which recognize total DNA from intact chromosome(s) free of aberrations, and which are derived from one or more different chromosomes. The hybridization pattern of test sample can then be compared with the hybridization pattern of said panel with normal chromosomal DNA to determine if there are any differences. A different hybridization pattern indicates the existence of one or more aberrations in the test chromosomal DNA.

So long as sufficient information is available about the members of the panel of probes employed, the nature of the specific aberration observed can be determined by correlating the specific differences observed between the control and test hybridization patterns with the particular probe(s) which hybridizes differently in each sample.

Probes employed in the practice of the present invention can be prepared employing a variety of vehicles, such as, for example, cosmids, yeast artificial chromosomes [see, for example, Burke et al., in Science 236: 806–4312 (1987)], F1plasmids [see, for example, O'Connor, et al., in Science 244: 1307–1312 (1989)], P1 bacteriophage [see, for example, Sternberg in Proc. Natl. Acad. Sci. U.S.A. 87: 103–107 (1990)], and the like. Construction of cosmid libraries, for example, has been described by Evans, et al., in Gene 79: 9–20 (1989). For example, cosmid vector sCos-1 has been prepared by digesting pWE15 DNA [described by Evans and Wahl in Methods Enzymol. 152: 604–610 (1987)] with ClaI+SalI and purifying the resulting 6 kb ClaI-SalI fragment which lacks the cos sequence. Cosmid pDVcos134 was digested with ClaI+XhoI, and a fragment containing the duplicated cos region was purified on an LPM agarose gel. The purified fragments were ligated using T4 DNA ligase and transformed into host strain DH5.

Genomic libraries can be constructed in cosmid vector(s) such as, for example, sCos-1, which contains duplicated cos sites for high efficiency microcloning, T3 and T7 bacteriophage promoters flanking the unique BamHI cloning site, two NotI sites for the excision of genomic inserts, a selectable gene (SV2-neo') for mammalian gene transfer, and a ColEl origin of replication. Detailed restriction maps of the cosmid insert in this vector may be rapidly determined by an end-labeling mapping procedure using T3- or T7-specific oligonucleotides.

The genomic cosmid library used in this study consisted of $1.5 \times 10^7$ independent clones and was constructed by using genomic DNA digested to an average size of 100–120 kilobases with MboI, dephosphorylated with calf intestinal phosphatase, ligated with sCos-1 DNA, and packaged with Gigapak Gold (Stratagene) in vitro packaging lysate. Only nonamplified libraries were used, and cosmid clones were archived in 96-well microtiter plates stored at −70° C. in LB media with 15% (vol/vol) glycerol and kanamycin sulfate at 25 $\mu$g/ml.

Specific probes which are useful in the practice of the present invention include cosmids c108, c116, and c4; plasmid p4.3, and the like (see FIG. 1). As an alternative to hybridization analysis, PCR probes can be derived from the unique sequences of the human *trithorax* gene and can be used for amplification of *trithorax*-encoding sequences. Exemplary PCR probes include any sequence of at least 15 contiguous nucleotides selected from Sequence ID Nos. 1, 2 3 or 4. Preferred primers comprise at least 20 contiguous nucleotides. Exemplary primer pairs include one sense primer and one anti-sense primer derived from:

nucleotides 191–215 (or complement thereof), inclusive, and nucleotides 760–786 (or complement thereof), inclusive, as set forth in SEQ ID NOS: 1 or 2; or nucleotides 4129–4152 (or complement thereof), inclusive, and nucleotides 4697–4723 (or complement thereof), inclusive, as set forth in SEQ ID NO: 4;

nucleotides 390–412 (or complement thereof), inclusive, and nucleotides 812–837 (or complement thereof), inclusive, as set forth in SEQ ID NOS: 1 or 2; or nucleotides 4327–4349 (or complement thereof), inclusive, and nucleotides 4749–4774 (or complement thereof), inclusive, as set forth in SEQ ID NO: 4;

nucleotides 501–519 (or complement thereof), inclusive, as set forth in SEQ ID NOS: 1 or 2, and nucleotides 1424–1450 of SEQ ID NO: 1 (or complement thereof), inclusive; or nucleotides 203–229 (or complement thereof), inclusive, as set forth in SEQ ID NO: 3; or nucleotides 4438–4456 (or complement thereof), inclusive, and nucleotides 5981–6006 (or complement thereof), inclusive, as set forth in SEQ ID NO: 4;

and the like.

A variety of techniques can be employed in the practice of the present invention, for example PCR, Southern blot, chromosomal in situ suppression hybridization (as recently described in *Science* 247:64–69 (1990), referred to hereinafter as "CISSH"), and the like can be employed. Similar techniques which can also be employed in the practice of the present invention have been described by Lawrence et al., in Cell 42: 51–61 (1983); Pinkel at al., in Proc. Natl. Acad. Sci. U.S.A. 83: 2934–2938 (1986); Pinkel et al., in Proc. Natl. Acad. Sci U.S.A. 85: 9138–9142 (1988); and Trask et al., in Genomics 5: 710–717 (1989).

Cell samples to be analyzed by CISSH can be employed directly without any particular preparation, or they can be subjected to conditions which promote growth, then arrested at metaphase [as described, for example, by Yunis and Chandler in *Clinical Diagnosis and Management by Laboratory Methods*, J. G. Henry, ed. (Saunders, Philadelphia) 16th Ed., pp 801–856 (1979)].

CISSH is carried out as follows. 20 to 50 ng of labeled probe DNA is combined with 1.5 to 3 µg of human placental DNA and sufficient salmon sperm DNA to obtain a total of 10 µl of hybridization cocktail. After denaturation of the probe mixture (75° C. for 5 min), preannealing of repetitive DNA sequences is allowed for 5 to 15 min (37° C.) before application to separately denatured chromosome specimens.

Alternatively, in cases where no suppression and therefore no competitor DNA is needed, probe mixtures are denatured and then cooled on ice. When cosmid signals are obtained in parallel with a specific decoration (i.e., a specific label) of chromosome 11, 300 ng of pooled, labeled inserts from a chromosome 11 library is combined with the differentially labeled cosmid DNA probe. For delineation of human chromosome 11, the total DNA inserts of the library LAllNS02 derived from sorted chromosome 11 [M. A. VanDilla, et al., *Biotechnology* 4:537 (1986)] were prepared as described by Lichter, et al., *Human Genetics* 80:224 (1988). To obtain Alu banding simultaneously with the probe signal, the competitor DNA is substituted by 300 ng of differentially labeled pBS-Alu4, and preannealing is reduced to a few seconds.

Alternatively, 100 ng of labeled pBS-Alu4 is denatured in hybridization cocktail, cooled on ice, and combined with a preannealed probe just before application to slides. After overnight incubation and posthybridization washes [see Lichter, et al., supra] the specimens are incubated with blocking solution [3% bovine serum albumin (BSA), 4×SSC (saline sodium citrate) or, when BSA cross-reacting DNP antibodies (anti-DNP) are used, 5% nonfat dry milk, 4×SSC] for 30 to 60 min at 37° C.

For detection, all protein reagents are made up in 1% BSA, 4×SSC, and 0.1% Tween 20 (BSA cross-reacting antibodies are preincubated in this solution for 30 min. at 37° C.) and then incubated with the specimen (37° C., 30 min) and followed by washes (4×SSC, and 0.1% Tween 20, three times for 3 min. at 42° C.). Biotin-labeled probes detected by incubation with fluorescein isothiocyanate (FITC)-conjugated avidin (DCS grade; 5 µg/ml; available from Vector Laboratories, Burlingame, Calif.) or Texas Red™ isothiocyanate (TRITC)-conjugated ExtrAvidin (5 µg/ml) (Sigma). The signal of some short DNA probes (for example, pT24-Hras) is amplified as described by D. Pinkel et al., in *Proc. Natl. Acad. Sci. U.S.A.* 83:2934 (1986). DNP-labeled probes are detected by incubation with rabbit-anti-DNP (7 µg/ml) (Sigma) and a second incubation with FITC- or rhodamine-conjugated goat-anti-rabbit antibodies (8 µg/ml) (Boehringer Mannheim). Digoxigenin-labeled probes are incubated first with sheep-anti-digoxigenin Fab fragments (2.5 µg/ml) (Boehringer Mannhein) and then with FITC-conjugated donkey-anti-sheep antibodies (7 µg/ml) (Sigma).

For single probe hybridizations, labeled DNA is detected by FITC-conjugates, and chromosomal DNA is counterstained by propidium iodide (PI) (200 ng/ml PI in 2×SSC, 5 min at room temperature). For hybridizations with multiple differentially labeled probes, chromosomal DNA is counterstained [see Lichter et al., supra] or banded [D. Schweizer, *Hum. Genet.* 57:1 (1981)] with diamidinophenylindole (DAPI).

After mounting in antifading solution [see Lichter et al; supra] the slides are evaluated on a Nikon Optiphot microscope equipped for conventional epifluorescence microscopy. For fine mapping, a modified version of the Bio-Rad laser scanning confocal microscope (Lasersharp MRC 500) is used in the photon counting mode (integration period of 0.1 to 0.3 ms per pixel) to produce digital images. The 488-nm line from an argon ion laser is used for excitation. In dual label experiments narrow band pass filters are used to obtain separate images of each fluorochrome (550 -nm filter for FITC; 610 -nm filter for PI or rhodamine). In some cases, the 532 -nm line from an Amoco Microlaser [frequency-doubled diode-pumped Nd:YAG (yttrium-aluminum-garnet)] is used to excite rhodamine. The two separate images of one object are stored and then overlayed electronically. For image optimization, digital filtering is applied. Photographs can be taken from the video screen.

Evidence of a defect in the gene encoding human *trithorax* peptide is readily obtained in a variety of way, e.g., by detecting the occurrence of a translocation which results in disruption of said gene. This can be detected, for example, by PCR amplification of a portion of the gene encoding human *trithorax* peptide using PCR primers derived from unique sites located both centromeric and telomeric of the translocation breakpoint. Exemplary primers useful for this purpose include polynucleotides having at least 15 contiguous nucleotides derived from SEQ ID NOS: 1, 2, 3 or 4, as described above.

Alternatively, evidence of a defect in the gene encoding human *trithorax* peptide can be obtained by hybridization of DNA derived from wild-type human *trithorax* gene region to a Southern blot of DNA obtained from the subject. As yet another alternative, evidence of a defect in the gene encoding human *trithorax* peptide can be obtained by in situ hybridization of DNA encoding wild-type human *trithorax* peptide to DNA obtained from the subject.

As a still further alternative, where translocation produces a hybrid protein (characterized by containing a portion of the amino acid sequence of the human *trithorax* protein, and a portion of a second protein derived from the locus with which chromosome 11 cooperates in undergoing translocation), evidence of a defect in the gene encoding human *trithorax* peptide can be obtained by evidence of the production of such a hybrid protein. Such hybrid proteins can be detected in a variety of ways, such as, for example, by immunoblot analysis.

Similarly, evidence of a defect in the gene encoding human *trithorax* peptide can be obtained by evidence of the production of a hybrid nucleic acid encoding such protein. Such hybrid nucleic acids can be detected in a variety of ways, e.g., by PCR.

The invention will now be described in greater detail by reference to the following non-limiting examples.

EXAMPLES

The following general procedures and resulting compositions are used throughout the Examples.

Yeast Artificial Chromosome and Cosmid Cloning

Yeast artificial chromosome human genomic libraries were generously supplied by M. Olson (St. Louis; see Browstein et al., in Science 244:1348–1351 (1989)) and D. Cohen (CEPH, Paris; see Albertsen et al., in Proc. Natl. Acad. Sci. 87:4256–4260 (1990)) and screened by PCR amplification of DNA pools [Green and Olson, Proc. Natl. Acad. Sci. USA Vol. 87:1213–1217 (1990)]. YAC clones were characterized by pulsed field electrophoresis and hybridization analysis, and in the case of clone B22B2, which contained two different YAC clones within the same yeast, were subsequently purified to a single colony by recloning, yielding B22B2L and B22B2S.

Cosmids were isolated by hybridization of gel purified YAC DNA to high density chromosome-specific cosmid libraries using phenol emulsion reassociation (PERT) hybridization [Djabali et al., Nucleic Acids Res. Vol. 20:6166 (1990)], or by subcloning the yeast containing YAC DNA into cosmid vector sCos-1 (Stratagene).

Yeast DNA was analyzed by restriction mapping and subcloning into cosmids. Thus, yeast DNA was partially digested with the enzyme Sau3A resulting in fragments of 10–50 kb. Fragments were size-fractionated by centrifugation through a 5–25% sucrose gradient for 17 hours, 22,000 rpm. Fractions containing fragments between 30–45 kb were pooled and 1 μg was ligated to 2 μg of BamHI digested sCos 1 vector. Cosmid DNA was packaged using the Gigapack Gold packaging extract (Stratagene). The total library of 15,000 clones was screened with total human DNA. One hundred twenty-five clones containing human inserts were digested by EcoRI, run on a 0.7% agarose gel, transferred on to GeneScreen membranes and used for cosmid walking experiments.

Contigs were constructed by comparing restriction enzyme digestion patterns using enzymes EcoRI, BamHI and NotI and by hybridization of the cosmids to RNA probes derived from the end of each cosmid with the T7 and T3 RNA polymerase (Stratagene).

Fluorescence in Situ Suppression Hybridization (FISSH)

In situ hybridization was carried out using normal human fibroblasts (CRL1634; Human Genetic Mutant Cell Repository, Camden N.J.) or the cell line RS4;11 [see Kearney et al., "Chromosome 11 q23 translocations in both infant and adult acute leukaemias are detected by in situ hybridization with a yeast artificial chromosome", in Blood, in press (1992)], carrying the t(4;11) translocation as described by Selleri et al., in Proc. Natl. Acad. Sci. USA Vol. 88:887–891 (1990)].

DNA Sequence Analysis

DNA sequence analysis was carried out by subcloning restriction fragments into plasmid vector Bluescript (Stratagene) and nested templates were created using ExoIII/Mung-bean nuclease (Stratagene). Sequencing was carried out using an ABI 373A automated DNA sequencer. Sequences were assembled using Staden DNA sequence analysis programs running on a SUN Sparcstation. Protein sequences were compared with the Genbank databases using the BLAST program [see Stephen in J. Mol Biol. 215:403–410 (1990)].

cDNA Library Screening

A KpnI-EcoRI fragment derived from p4 was used ELS a probe to screen a human cortex cDNA library (Stratagene; see Example 3). $10^6$ pfu (plaque forming units) were plated and screened by standard techniques [Benton and Davis, Science Vol. 196:180–182 (1977)], and a single positive clone was identified. Using the Exassist/solr system (Stratagene) this clone was excised into plasmid Bluescript (pBS; Stratagene).

Example 1

Molecular Map of the 11 q23 Breakpoint Region

To isolate translocation breakpoints of chromosome 11 q, a physical landmark map was constructed for human chromosome 11, using chromosome 11-specific cosmids prepared from somatic cell hybrids or flow sorted human chromosomes [see Evans and Lewis, Proc. Natl. Acad. Sci. USA Vol. 86:5030–5034 (1989)], and high resolution fluorescence in situ hybridization [see Lichter et al., Science Vol. 85:64–68 (1990)]. The t(4;11) breakpoint was found to be located in the interval separating the CD3 and Thy-1 genes on chromosome 11 q23 [see, for example, Rowley et al. supra, Chen et al., Blood Vol. 78:2498–2504 (1991)].

Sequence tagged sites (STSs) corresponding to the cosmid landmarks were established and used to isolate yeast artificial chromosomes from a human genomic YAC library [see, for example, Browstein et al., Science Vol. 244:1348–1351 (1989)]. A YAC designated B22B2L was isolated as described by Rowley et al. supra, and shown to contain a portion of the CD3 gene complex extending telomeric from the CD3 ε gene. Since this YAC clone was found to be inherently unstable, an additional YAC clone (CEPH 141G12) containing the breakpoint region was isolated from the CEPH YAC library [Albertsen et al., Proc. Natl. Acad. Sci. USA Vol. 87:4256–4260 (1990)] and used as a control for the integrity of YAC B22B2L. DNA probes prepared from landmark cosmids were used to locate the chromosome translocation breakpoint telomeric to the CD3 gene (see FIGS. 1 and 2).

Figure 1B:
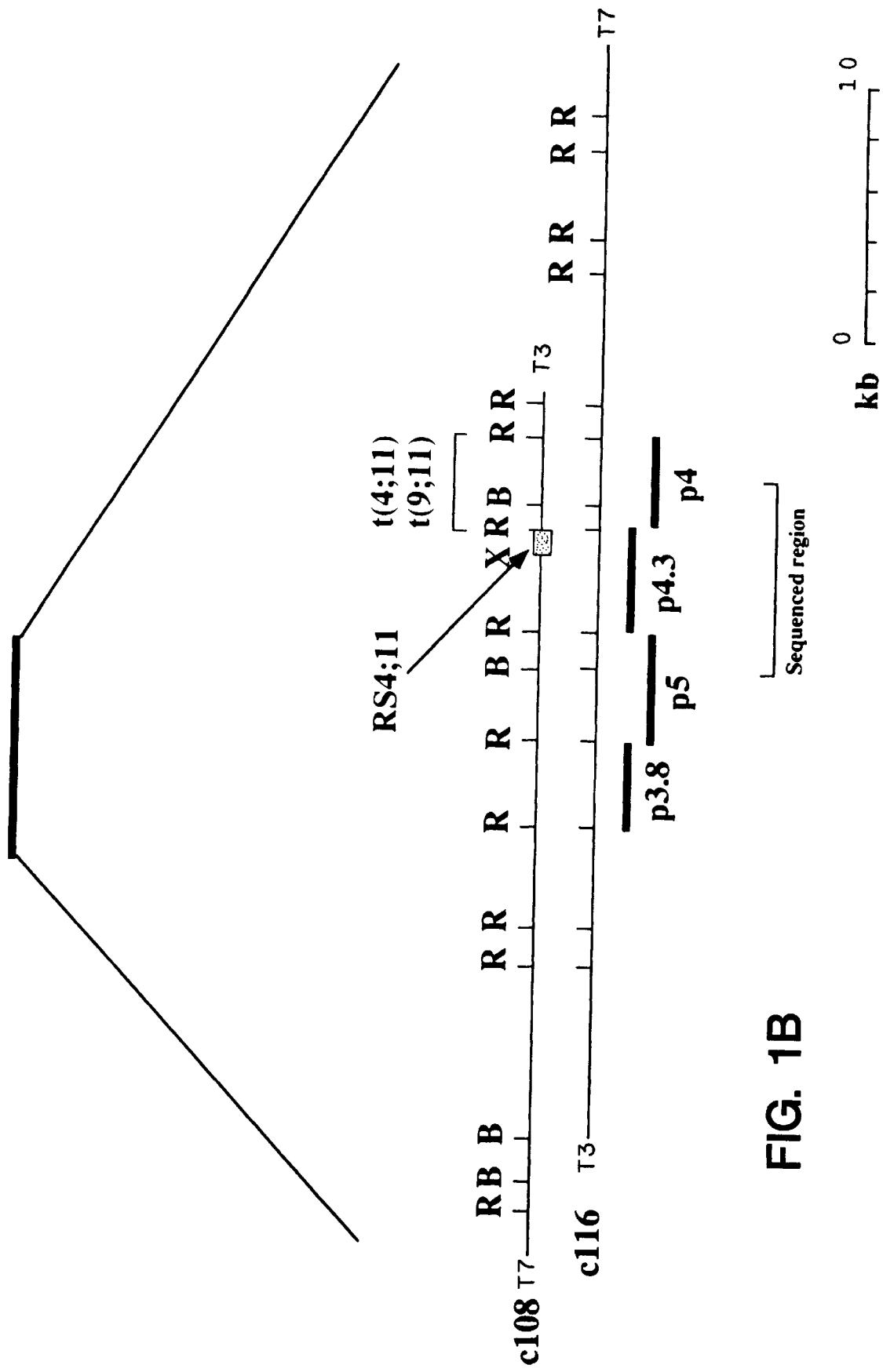
FIG. 1B shows cosmid clones c108 and c116, and a detailed restriction map thereof (R=EcoRl; X=XtaI; B=BamHI). EcoRl fragments subcloned into plasmid vector Bluescript for use as probes and for DNA sequence analysis result in subclones p3.8, p5, p4.3 and p4. The region of clones c108 and c116 subjected to DNA sequence analysis is indicated in the Figure. The complete DNA sequence of fragment p4.3 was determined using nested deletions derived from cosmid subclones p4, p5 and p4.3 as sequence templates.

By using fluorescence in situ hybridization, cosmid clones c108 and c116 were identified as containing the RS4;11 translocation breakpoint (see FIG. 1B). In addition, a detailed restriction map was determined by oligo-end labeling using T3 and T7 promoters present in the cosmid vector flanking the insert [Evans and Lewis, supra]. Moreover, the location of the t(4;11) and t(9;11) breakpoints in a number of patients and the RS4;11 cell line were determined by Southern blot analysis (R=EcoRI; X=XbaI; B=BamHI). EcoRI fragments were subcloned into the plasmid vector Bluescript for use as probes and for DNA sequence analysis, resulting in subclones p3.8, p5, p4.3 and p4. The region subjected to DNA sequence analysis is indicated in the figure.

Using fluorescence in situ hybridization, YAC clone B22B2L has previously been shown to contain the chromosome translocation breakpoint and to hybridize to both derivative chromosomes in the RS4;11 cell line carrying the t(4;11) translocation, and in leukaemic cells from ALL and AML patients [Rowley et al., supra] with the t(4;11), t(9;11), t(6;11) and t(11;19) translocations.

In order to further characterize this region of chromosome 11 q23 and to identify transcripts whose expression might be affected by these chromosome rearrangements, a cosmid contig was constructed by subcloning the B22B2L YAC DNA directly into vector sCOS-1 [see Evans and Wahl, supra], or by PERT hybridization [Djabali et al., supra] of purified YAC DNA to high density arrays of chromosome 11-specific cosmids [see Evans et al., supra]. A physical contig map spanning more than 360 kb was constructed (see FIG. 1). The t(4;11) rearrangement was detected by pulsed field gel electrophoresis and by Southern blot analysis. Southern blot analysis was employed to localize the t(4;11) breakpoint to a region contained within cosmid c108 and c116 (FIG. 1) using DNA isolated from the RS4;11 and human placenta DNA digested with PstI and XbaI. The probe was an XbaI-KpnI fragment of subclone p4 (FIG. 1). Size markers employed were HindIII fragments of bacteriophage lambda. The breakpoint was localized to the region covered by cosmids c108 and c116, about 115 kb telomeric to the CD3 γ chain gene (see FIG. 1).

Because of the repetitive nature of probes isolated from this region, fluorescence in situ suppression hybridization (FISSH) was carried out using cosmid clones c62, c108 and c4 (see FIG. 1) to precisely define the location of the RS4;11 breakpoint as being within the cosmid contig on RS4;11 chromosomes. Cosmid clone c62 shows hybridization signals on the normal chromosome 11 and on the derivative chromosome 11, and is, therefore, localized centromeric to the 11 q23 breakpoint. Cosmid clone c4 shows hybridization signals on the normal chromosome 11 and on the derivative chromosome 4, and is, therefore, localized telomeric to the 11 q23 breakpoint. Cosmid clone c108 shows hybridization signals on normal chromosome 11 and on both derivative chromosomes 4 and 11. Similarly, hybridization signals were detected on both derivative chromosomes 4 and 11 with cosmids c108 and c116, using chromosomes prepared from cell line RS4;11.

The resulting map reveals the presence of four potential HTF (i.e., "HpaII-tiny fragment") islands suggested by location of clusters of CpG-rich restriction sites (see the cluster of B, E and S restriction sites (wherein B=BssHII; E=EagI; and S=SacII); the cluster of M, S, B, N, S, and N restriction sites (wherein M=MluI and N=NotI; the cluster of N, B and B restriction sites and the cluster of E, B, C and F restriction sites in FIG. 1; wherein C=ClaI and F=StiI)). The CpG cluster located nearest to the breakpoint, defined by a NotI and BssHII site contained within cosmid c62, was subsequently shown to be hypomethylated in the genome and to represent an authentic HTF island.

In order to detect and define genes located near this breakpoint, unique copy probes were prepared from cosmids containing and flanking the breakpoint as follows. Human DNA inserts from the cosmids referred to above were subcloned into a plasmid vactor such as Bluescript, screened with human repetitive sequences ($C_0t$-1 DNA), and selected for sequences which did not hybridize with the repetitive sequences.

These probes were used for the detection of evolutionarily conserved sequences and for detection of mRNA transcripts.

Unique copy probes from cosmid c108 (subclone p3.8) and c13 (subclone p500) detect cross-hybridizing sequences among primates, cow and pig, indicating the presence of evolutionarily conserved and potentially coding sequences located on either side of the breakpoint. Potential genes located in the vicinity of the t(4;11) breakpoint were detected using hybridization of unique copy DNA fragments derived from the cosmids shown in FIG. 1, with "zoo" blots containing genomic DNA from various species. For example, a fragment from cosmid c13 (p500) detected cross-hybridization with cow, pig, rabbit and rodent DNAs. A unique copy probe derived from cosmid c108 subclone p3.8 detected cross-hybridization with primate, pig and rodent genomic DNA.

Example 2

Detection of mRNA Transcripts

Whole cosmid DNA or unique copy DNA probes derived from cosmid subclones detected two mRNA transcripts in the region immediately flanking the translocaticn breakpoint. A transcript of approximately 11.5 kb was detected in heart, lung and brain, as well as T and B lymphocytes, using cosmid c108. Transcribed sequences were detected on Northern blot using unique copy probe derived from cosmids shown in FIG. 1. A unique copy probe derived from cosmid 108 (fragment Xba-EcoRl of p4) detects an 11.5 kb transcript in RNA derived from human heart, lung and brain. An additional transcript of 4.4 kb was detected in several tissues, and most intensely in placenta, pancreas, liver and kidney, using unique copy probes derived from cosmid c67.

This analysis establishes the location of two transcribed sequences located in the immediate vicinity of the t(4;11) breakpoint. The 11.5 kb transcript was also detected using cosmid c108, spanning the breakpoint, as a probe and with unique copy subclones of cosmid c108 located on each side of the breakpoint.

Example 3

DNA Sequence of the Translocation Breakpoint

A portion of cosmid c108 spanning the t(4;11) breakpoint was subcloned into the plasmid vector Bluescript and the DNA sequence determined. The DNA sequence of 6 kb containing the translocation breakpoint (see FIG. 2A) was found to consist of more than 80% repetitive DNA sequences, including 9 Alu-repetitive elements [see, for example, Deininger et al., in J. Biol. Chem. 151:17–31 (1981)] and an element homologous to a segment of the LINE-1 repetitive element [see, for example, Shafit-Zagardo, et al., in Nucleic Acids Research 10:3175–3193 (1982)]. Unique sequences of 110, 120 and 180 bp, which did not define obvious open reading frames, separated the groups of repeats. Southern blot analysis using non-repetitive probes localized the t(4;11) breakpoint of the RS4;11 cell line to within a 1.2 kb XbaI-EcoRI fragment consisting almost entirely of Alu sequences.

The DNA sequence also revealed two regions of unique sequence with potential open reading frames located approximately 3 kb centromeric to the breakpoint and 4 kb telometric to the breakpoint. The protein sequence defined by these open reading frames was compared against known protein sequences using the computer program BLAST [see Stephen, in J. Mol. Biol. Vol. 215:403–410 (1990)]. A region of 150 bp located immediately centromeric to the EcoRI site of clone p5 (FIG. 2B) showed an extended open reading frame with highly significant similarity with the protein product of the *trithorax* gene of Drosophila [Mazo et al., supra], with a Poisson probability of 0.0017 (FIG. 2B). The second open reading frame, located telometric to the breakpoint, revealed additional sequence similarity with the *trithorax* protein with a Poisson probability of 0.0012 (FIG. 2B). Amino-acid sequence comparison revealed that the homologies were located within the zinc finger motifs 2 and 6a of the *trithorax* gene (FIG. 2B).

To confirm that the open reading frames corresponded to authentic mRNA transcripts, Northern blot analysis using PCR products derived from each of these sequences was carried out. Probes from each open reading frame independently detected the 11.5 kb mRNA transcript, suggesting that these sequences represent exons of a large *trithorax*-like gene spanning the breakpoint.

In order to further characterize this transcript, a genomic fragment corresponding to ORF2 (Fragment KpnI-EcoRI of p4) was used to isolate cDNA clones from a human brain cDNA library. A partial cDNA clone of 3 kb was isolated and the DNA sequence of the portion corresponding to ORF2 determined. This sequence revealed an open reading frame with highly significant sequence similarity to the *Drosophila trithorax* gene product (FIG. 2B) and demonstrates complete conservation of all of the cysteine residues which form a zinc finger-like structure. Thus, it is concluded that the gene spanning the t(4;11) breakpoint (denoted Htrxl) encodes a protein with a high degree of sequence homology to the *Drosophila trithorax* gene and is therefore likely to encode a mammalian transcriptional regulatory factor.

The complete sequence of this 3 kb partial cDNA clone has been determined and is presented as residues 3944–6982 in SEQ ID NO: 4. This sequence information has been deposited with Genbank (Accession No. L01986).

Example 4

Analysis of t(4;11) and t(9;11) Breakpoints in Patients

To determine the consistency of the breakpoint in different patients with t(4;11) ALL and t(9;11) AML rearrangements, DNA from adult leukaemic patients and from cell line RS4;11 were evaluated by Southern blotting using unique copy probes (prepared as described in Example 1) which flank the RS4;11 breakpoint. Patient DNA was digested with BamHI, EcoRI, and XbaI, and subjected to Southern blot analysis, using single copy probes isolated from cosmid c108. The 1 kb XbaI-EcoRI probe isolated from the 3.8 kb EcoRI fragment reveals an 18 kb non-rearranged BamHI fragment in the RS4;11 cell line as well as in leukaemic cells from t(4;11) and t(9;11) patients. The XbaI-EcoRI probe isolated from clone p4 reveals a 15 kb non-rearranged BamHI fragment. These results indicate that in the RS4;11 cell line, in t(4;11) leukaemic cells, and in t(9;11) leukaemic cells, all of the breakpoints are contained within the same 9 kb BamHl fragment of cosmid 108.

DNA derived from 8 infant leukaemia patients was digested with EcoRI and evaluated by Southern blot hybridization using the 1 kb XbaI-EcoRI probe. This analysis revealed rearrangements in one t(9;11) leukaemic patient and three t(4;11) leukaemia patients, and suggests that, in this small series, all of the breakpoints are located within the same 5 kb region. The EcoRI (p4) fragment is not rearranged in the RS4;11cell line and therefore the breakpoint can be further localized in this cell line to within a 1.2 kb XbaI-EcoRI fragment consisting entirely of Alu elements. Due to the repetitive nature of this sequence, the precise location of the breakpoint cannot readily be determined.

Example 5

Genomic Structure of Htrx1 Around the Breakpoints

The intron-exon structure of the partial cDNA spanning the breakpoints was established using the different EcoR1 fragments of the cDNA as probes on cosmid 116 digested by EcoR1, BamH1 and BamH1/EcoR1. This approach determined the minimum number of introns contained within the 3 kb cDNA. In order to define exactly the position and length of each of these introns direct sequencing of the cosmid was performed using oligonucleotides defined on the cDNA sequence. These results are summarized in FIG. 3.

Example 6

Patient Studies

Clustering of the breakpoints on chromosome 11 q23 has been demonstrated in infant leukaemic patients with t(4;11) and t(9;11) translocations using genomic probes derived from cosmids spanning the region [see Mazo et al., in Proc. Natl. Acad. Sci. USA 87:2112–2116 (1990); Cimino et al., in Cancer Research 51:6712–6714 (1991); Ziemin-van der Poel et al., in Proc. Natl. Acad. Sci. USA 88:10735–10739 (1991); and Cimino et al., in Cancer Research 52:3811–3813 (1992)]. The 3 kb cDNA used as a probe on Southern blots of adult leukaemia cell DNA detects rearrangements in patients with t(4;11) [6 of 7 patients studied], t(6;11) [2 of 2 patients studied], t(9;11) [1 of 1 patient studied] and t(10;11) [1 of 1 patient studied] with the enzyme EcoRI (FIG. 3; Table). The single patient (number 7) with t(4;11) in whom the rearrangement was not demonstrated showed the rearrangement with a more centromeric probe. The breakpoints in the two cell lines RS4;11 and Karpas 45 containing t(4;11) and t(X;11) respectively have been mapped more precisely using a number of restriction enzymes and EcoRI fragments of the cDNA. In these cell lines the breakpoints lie in two different introns and are separated by approximately 5 kb (see FIG. 3).

TABLE 1

| Patient | Age | Sex | Leukaemia | Karyotype |
|---|---|---|---|---|
| 1* | 79 | F | ALL-L2 | 46, XX, t(4;11)(q21;q23). |
| 2 | 13 | F | ALL-L2 | 46, XX, t(4;11)(q21;q23). |
| 3 | 43 | M | ALL-L2 | 46, XY, t(4;11)(q21;q23). |
| 4 | 53 | F | ALL-L2 | 46, XX, t(4;11)(q21;q23). |
| 5 | 40 | F | ALL-L2 | 46, XX, t(4;11)(q21;q23), add (7)(p1?), add (9)(p1?), add(17)(p1?), −19 |
| 6* | 44 | F | ALL-L2 | 51, XX, +X, +1, +4, t(4;11)(q21;q23), |

TABLE 1-continued

| Patient | Age | Sex | Leukaemia | Karyotype |
|---|---|---|---|---|
| 7 | 28 | M | ALL-L2 | +8, der(18), t(17;?)(q10;?), +21. 52, XY, +X, +add(3)(g?), t(4;11)(q21;q23), +6, +13, +15, inc. |
| 8* | 52 | M | AML-M4 | 46, XY, t(6;11)(q27;q23). |
| 9* | 45 | M | AML-M4 | 46, XY, dir ins (6;11)(q27;q13q23). |
| 10* | 59 | F | tAML-M1 | 46, XX, t(9;11)(p22;q23). |
| 11* | 27 | M | AML-M5 | 46, XY, t(10;11)(p12;q23). |
| RS4:11§ | <1 | F | ALL-L2 | 46, XX, t(4;11)(q21;q23), i(7)(q10). 91, Y, −X, −X, −Y, t(1;5)(q25;q13). |
| Karpas 45¶ | 7 | M | T-All | der(11)t(X;11)(q13;q23), t[der(11)t(X;11)(q13;q23);14][p15;q11]. |

Described in
*Kearney et al., Blood 80:1659–1665 (1992),
§Strong et al., Blood 65:21–31 (1985),
¶Karpas et al., Leukemia Research 1:35–49 (1976)

Example 7

Htrx Expression

The expression of Htrx1 in cell lines of lymphoid origin was assessed by Northern analysis. Total RNA from T and B lymphocyte lines representing various differentiated states were separated, transferred onto membrane and Htrx-specific sequences detected using the 3 kb cDNA as a probe. Three transcripts of 15, 12.5 and 11.5 kb were detected in the mature T cell lines, Jurkat and HUT78, as well as the immature T cell line CEM. Likewise, all three transcripts were expressed in the IgM-secreting B cell line Namalwa. In contrast only the largest transcript was present at detectable levels in the murine pre-B-like cell line 70/3. 70/3 cells can be induced to progress towards a more mature B cell phenotype by treatment with bacterial lipopolysaccharide (LPS) (Paige, et al., Nature, 292:631–633 (1980)). Six hours of treatment with a final concentration of 10 μg/ml LPS upregulates the level of the 15 kb Htrxl transcript and stimulates the expression of the 12.5 kb mRNA. In addition, the expression of Htrxl was analyzed in normal human adult tissues, transcripts were detected in brain, pancreas, liver, lung, heart, kidney, skeletal muscle, but were absent in placenta.

While the invention has been described in detail with reference to certain preferred embodiments thereof, it will be understood that modifications and variations are within the spirit and scope of that which is described and claimed.

Summary of Sequences

SEQ ID NO: 1 is a substantial portion of the DNA sequence for the human *trithorax* gene (htrx).

SEQ ID NO: 2 is the 5' portion of the ~3 kb CDNA encoding the human *trithorax* gene (htrx). The sequence of the ~3 kb partial clone of htrx has been deposited in Genbank as accession number LO1986.

SEQ ID NO: 3 is the 3' portion of the ~3 kb cDNA encoding htrx.

SEQ ID NO: 4 is the nucleotide sequence of a cDNA encoding the human *trithorax* (htrx), and the deduced amino acid sequence thereof.

SEQ ID NO: 5 is the deduced amino acid sequence of human *trithorax* (htrx).

SEQ ID NO: 6 is a genomic nucleotide sequence encoding ORF1 (see FIG. 2B), and the deduced amino acid sequence thereof.

SEQ ID NO: 7 is a portion of the human *trithorax* peptide upstream of the 11 q23 translocation breakpoint (see ORF1 in FIG. 2B).

SEQ ID NO: 8 is a portion of the *Drosophila trithorax* peptide corresponding to ORF1 (see SEQ ID NO:7).

SEQ ID NO: 9 is the deduced amino acid sequence of a portion of the human *trithorax* peptide downstream of the 11 q23 translocation breakpoint (see ORF2 in FIG. 2B).

SEQ ID NO: 10 is a portion of the Drosophila *trithorax* peptide corresponding to ORF2 (see SEQ ID NO:9).

SEQ ID NO: 11 is the deduced amino acid sequence derived from a CDNA derived from the genomic nucleic acid sequence which encodes the amino acid sequence set forth in SEQ ID NO: 5 (see ORF3 in FIG. 2B).

SEQ ID NO: 12 is a portion of the Drosophila *trithorax* peptide corresponding to ORF3 (see SEQ ID NO: 11).

That which is claimed is:

1. Isolated nucleic acid which contiguously encodes a human *trithorax* peptide having multiple zinc fingers, wherein the nucleic acid hybridizes under low stringency hybridization conditions to a nucleic acid molecule comprising the nucleotide sequence of SEQ ID NO: 1.

2. Nucleic acid according to claim 1, wherein said nucleic acid is DNA, cDNA, or RNA.

3. Isolated nucleic acid comprising SEQ ID NO: 1.

4. Isolated nucleic acid which encodes a peptide comprising a sequence selected from the group consisting of SEQ ID NO: 7, SEQ ID NO: 9 and SEQ ID NO: 11.

5. Nucleic acid according to claim 4, wherein said nucleic acid is DNA, cDNA, or RNA.

6. Isolated antisense nucleic acid comprising at least 20 contiguous nucleotides of the antisense sequence of SEQ ID NO: 1.

7. An isolated nucleic acid probe comprising at least 20 contiguous nucleotides of the nucleic acid of claim 3.

8. A nucleic acid probe selected from the group consisting of cosmid c108, cosmid c116, cosmid c4, and plasmid p4.3.

9. The probe of claim 7, comprising a nucleotide sequence selected from the group consisting of:

nucleotides 191 to 215 of SEQ ID NO: 1;

nucleotides 390 to 412 of SEQ ID NO: 1;

nucleotides 501 to 519 of SEQ ID NO: 1;

nucleotides 760 to 786 of SEQ ID NO: 1;

nucleotides 812 to 837 of SEQ ID NO: 1; and nucleotides 1424 to 1450 of SEQ ID NO: 1.

10. A primer pair, comprising nucleotide sequences selected from the group consisting of;

nucleotides 191 to 215 and nucleotides 760 to 786 of SEQ ID NO: 1;

nucleotides 390 to 412 and nucleotides 812 to 837 of SEQ ID NO: 1; and nucleotides 501 to 519 and nucleotide 1424 to 1450 of SEQ ID NO: 1.

* * * * *